United States Patent [19]

Angehrn et al.

[11] Patent Number: 5,981,519
[45] Date of Patent: Nov. 9, 1999

[54] VINYL-PYRROLIDINONE CEPHALOSPORINS

[75] Inventors: Peter Angehrn, Böckten; Paul Hebeisen, Basel, both of Switzerland; Ingrid Heinze-Krauss, Schliengen, Germany; Malcolm Page, Basel, Switzerland; Valérie Runtz, Rixheim, France

[73] Assignee: Hoffman-La Roche Inc., Nutley, N.J.

[21] Appl. No.: 08/986,549

[22] Filed: Dec. 8, 1997

[30] Foreign Application Priority Data

Dec. 19, 1996 [EP] European Pat. Off. ............... 96120472
Nov. 7, 1997 [EP] European Pat. Off. ............... 97119528

[51] Int. Cl.[6] ..................... A61K 31/545; C07D 501/24; C07D 501/56
[52] U.S. Cl. ........................ 514/202; 514/203; 540/222; 540/225
[58] Field of Search ................... 540/222, 225; 514/202, 203

[56] References Cited

U.S. PATENT DOCUMENTS 5,523,400  6/1996  Wei et al. ............................ 514/202

FOREIGN PATENT DOCUMENTS

| 0 408 034 | 1/1991 | European Pat. Off. . |
| 0 723 965 | 7/1996 | European Pat. Off. . |
| 0 774 466 | 5/1997 | European Pat. Off. . |
| WO 94/10177 | 5/1994 | WIPO . |
| WO 97/03990 | 2/1997 | WIPO . |

OTHER PUBLICATIONS

Heinze–Krauss, et al. J. Med. Chem. 39(9) 1996 pp. 1864–1871.
Green, T., "Protective Groups in Organic Synthesis", Chapter 7, pp. 218–287 (1981).

*Primary Examiner*—Mark L. Berch
*Attorney, Agent, or Firm*—George W. Johnston; Patricia S. Rocha-Tramaloni; Alan P. Kass

[57] ABSTRACT

The present invention relates to compounds having the formula

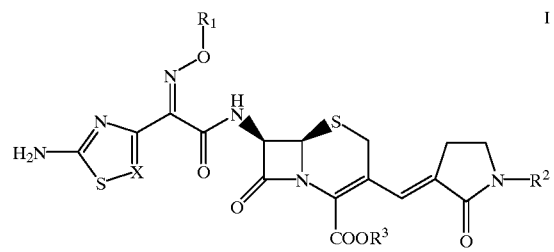

wherein X, $R^1$, $R^2$, $R^3$, $R^4$, $R^5$, $R^6$, and $R^7$ are as defined herein as well as readily hydrolyzable esters thereof, pharmaceutically acceptable salts of said compounds and hydrates of the compounds of formula I and of their esters and salts. These compounds have valuable pharmacological activity for the treatment and prophylaxis of infectious diseases, especially those caused by methicillin resistant *Staphylococcus aureus* (MRSA) and *Pseudomonas aeruginosa*.

65 Claims, No Drawings

VINYL-PYRROLIDINONE CEPHALOSPORINS

The present invention relates to compounds having the formula wherein
X is CH or N;
$R^1$ is hydrogen or cyclopentyl;
$R^2$ is selected from the group consisting of and $R^3$ is hydrogen, an alkalimetal ion or a tertiary ammonium group;
$R^4$ is hydrogen, an amino protecting group, pyrrolidin-2-ylmethyl, azetidin-3-ylmethyl, iminomethyl, or 1-carbamimidoyl;
$R^5$ is hydrogen, dialkylcarbamoyl, ω-hydroxyalkyl, ω-aminoalkyl, pyridinium-1-ylmethyl, 1-hydroxy-3-aminomethyl-propyl or (hydroxy)-(pyrrolidin-2-yl) methyl;
$R^6$ is hydrogen, trifluoromethyl or hydroxy; and
$R^7$ is alkyl, ω-hydroxy-alkyl, cycloalkyl, 3-pyrrolidinyl, 3-azetidinyl, iminomethyl or 1-carbamimidoyl;
as well as readily hydrolyzable esters thereof, pharmaceutically acceptable salts of said compounds and hydrates of the compounds of formula I and of their esters and salts.

Furthermore, the invention is concerned with making the compounds of formula I; with their use as pharmaceutically active substances, particularly for the treatment and prophylaxis of infectious diseases, and with pharmaceutical preparations containing a compound of formula I for the treatment and prophylaxis of infectious diseases, especially infectious diseases caused by methicillin resistant *Staphylococcus aureus* (MRSA) and *Pseudomonas aeruginosa*.

Preferred compounds of formula I are compounds wherein

X is CH or N;
$R^1$ is hydrogen;
$R^2$ is selected from the group consisting of formula and $R^3$ is hydrogen, an alkalimetal ion or a tertiary ammonium group;
$R^4$ is hydrogen, an amino protecting group, iminomethyl, or 1-carbamimidoyl;
$R^5$ is hydrogen or hydroxymethyl;
$R^6$ is hydrogen or hydroxy; and
$R^7$ methyl or 2-hydroxyethyl;

as well as readily hydrolyzable esters thereof, pharmaceutically acceptable salts of said compounds and hydrates of the compounds of formula I and of their esters and salts.

The compounds of the present formula I are useful in the treatment of infectious diseases caused by bacterial pathogens in particular methicillin resistent *Staphylococci aureus* (MRSA) and *Pseudomonas aeruginosa*.

In above compounds of formula I the $R^2$ substituted pyrrolidinone can be present in the E-form:

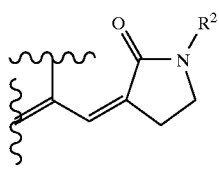

or in the Z-form:

Compounds of formula Ia, i.e. compounds wherein the pyrrolidinone is in the E-form are generally preferred.

The term "protected amino group" refers to groups such as those employed in peptide chemistry, such as an alkoxycarbonyl group such as tert-butoxycarbonyl, allyloxycarbonyl and the like; a substituted alkoxycarbonyl group such as trichloroethoxycarbonyl etc.; an optionally substituted aralkyloxycarbonyl group, for example, p-nitrobenzyloxycarbonyl or benzyloxycarbonyl; an aralkyl group such as trityl or benzhydryl; an alkanoyl group such as formyl or acetyl; a halogen-alkanoyl group such as chloroacetyl, bromoacetyl, iodoacetyl or trifluoroacetyl; or a silyl protective group such as the trimethylsilyl group.

Preferred amino protecting groups are tert-butoxycarbonyl (t-BOC), allyloxycarbonyl (ALLOC) and trityl.

Other examples of such groups may be found in and described in Green, T., Protective Groups in Organic Synthesis, Chapter 7, John Wiley and Sons, Inc. (1981), pp. 218–287, herein incorporated by reference.

As used herein, the term "alkyl" refers to both straight and branched chain saturated hydrocarbon groups having 1 to 8 and preferably 1 to 4 carbon atoms, for example, methyl, ethyl, n-propyl, isopropyl, tertiary butyl and the like.

As used herein, the term "cycloalkyl" refers to a saturated hydrocarbon ring having 3 to 9 carbon atoms. Examples include cyclopropyl, cyclopentyl, cyclohexyl, and the like.

As used herein, the term "ω-hydroxy-alkyl" refers to both straight and branched chain saturated hydrocarbon groups as defined above bearing a hydroxy group in the terminal position, e.g. hydroxymethyl, 2-hydroxyethyl, 3-hydroxypropyl, and the like.

As used herein, the term "ω-amino-alkyl" refers to both straight and branched chain saturated hydrocarbon groups as defined above bearing an amino group in the terminal position, e.g. aminomethyl, 2-aminoethyl, 3-aminopropyl, and the like.

As used herein pharmaceutically acceptable salts useful in this invention include salts derived from metals, salts from amino acids and salts of mineral or organic acids. Examples of preferred metal salts are those derived from the alkali metals, for example, lithium ($Li^+$), sodium ($Na^+$) and potassium ($K^+$), from the earth alkali metals, for example magnesium ($Mg^{++}$). Those salts derived from amino acids such as, for example, salts with arginine or lysine. Examples of salts of mineral acids are for example chlorides, sulphates or phosphates, and examples of salts of organic acids mesylates, napsylates, besylates, maleates, salicylates, tartrates, lactates, citrates, benzoates, succinates, acetates and the like. Especially preferred are chlorides, sulfates, phosphates, lactates or mesylates.

As readily hydrolyzable esters of the compounds of formula I there are to be understood compounds of formula I, wherein the carboxy group in 2-position is present in the form of readily hydrolyzable ester group. Examples of such esters, which can be of the conventional type, are the lower alkanoyloxy-alkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy)methyl ester; 2-[(2-methylpropoxy)carbonyl]-2-pentenyl ester; 1-[[(1-methylethoxy)-carbonyl]oxy]ethyl ester; 1-(acetyloxy) ethyl ester; (5-methyl-2-oxo-1,3-dioxol-4-yl) methyl ester; 1-[[(cyclohexyloxy)carbonyl]oxy]ethyl ester; and 3,3-dimethyl-2-oxobutyl ester. It will be appreciated by those of ordinary skill in the art that the readily hydrolyzable esters of the compounds of the present invention can be formed at a free carboxy group of the compound.

Examples of salts of the compounds of formula I are defined under "pharmaceutically acceptable salts" above.

A preferred embodiment of the invention are compounds of formula I wherein X is CH or N and $R^2$ represents a group

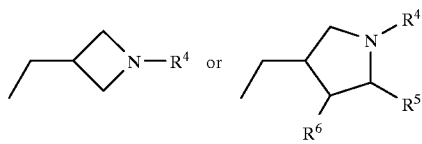

wherein $R^4$ is hydrogen, iminomethyl or 1-carbamimidoyl; $R^5$ is hydrogen or hydroxymethyl; and $R^6$ is hydrogen or hydroxy.

In another further preferred embodiment of the invention are compounds of formula I wherein X is CH or N and $R^2$ represents a group

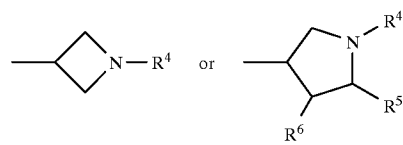

wherein $R^4$, $R^5$ and $R^6$ are as defined above.

Especially preferred are compounds of formula I wherein $R^5$ and $R^6$ are hydrogen.

An especially preferred embodiment of the invention are compounds of formula I, wherein X is CH and $R^2$ represents a group

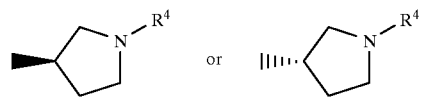

wherein $R^4$ is as defined above.

A further especially preferred group of compounds consists of compounds of formula I wherein X is N and $R^2$ represents a group

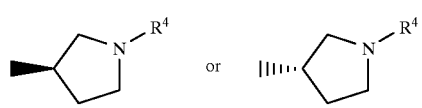

wherein R⁴ is as defined above.

A further preferred embodiment are compounds of formula I, wherein

X is CH or N
R¹ is hydrogen or cyclopentyl
R² is selected from the group consisting of

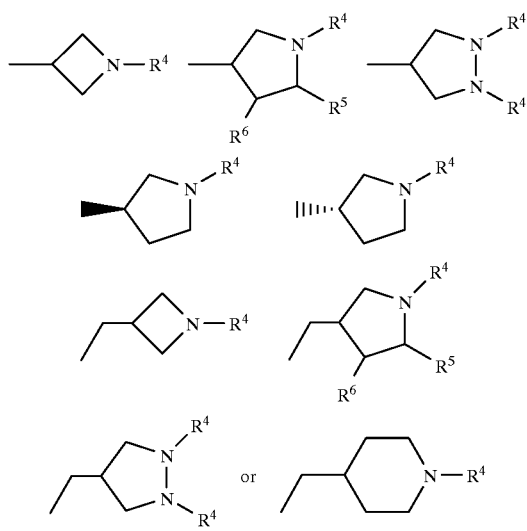

R³ is hydrogen, an alkalimetal ion or a tertiary ammonium group,
R⁴ is hydrogen or an amino protecting group;
R⁵ is hydrogen or dialkylcarbamoyl, and
R⁶ is hydrogen or trifluoromethyl, as well as readily hydrolyzable esters thereof, pharmaceutically acceptable salts of said compounds and hydrates of the compounds of formula I and of their esters and salts.

Other preferred embodiment are compounds of formula I, wherein

R² is selected from the group consisting of

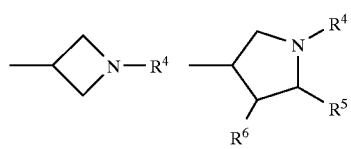

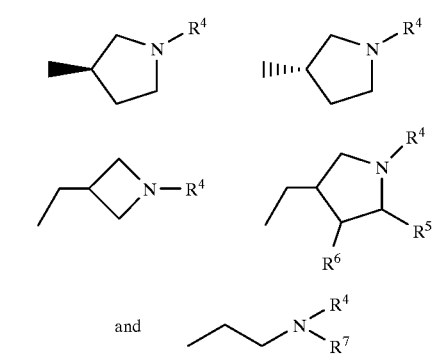

and X, R¹, R³, R⁴, R⁵, R⁶, and R⁷ are as provided for above.

Further additional preferred embodiments are compounds of formula I wherein

R² is selected from the group consisting of

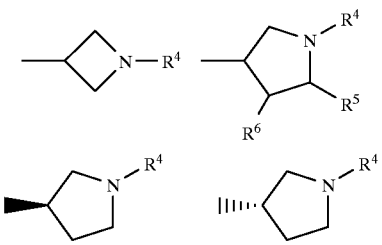

and X, R¹, R³, R⁴, R⁵, and R⁶ are as provided for above.

Especially preferred compounds are, for example,

A: (6R, 7R)-7-[(Z)-2-(5-Amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid

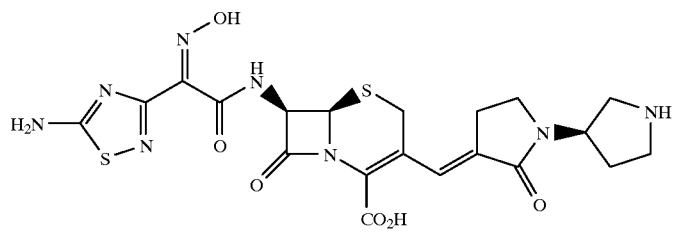

B: (6R, 7R)-7-[(Z)-2-(5-Amino-[1,2,4]thiadiazol-3-yl)-2-hydroxyimino-acetylamino]-8-oxo-3-[(E)-(S)-2-oxo-[1,3']bipyrrolidinyl-3-ylidenemethyl]-5-thia-1-aza-bicyclo[4.2.0]oct-2-ene-2-carboxylic acid

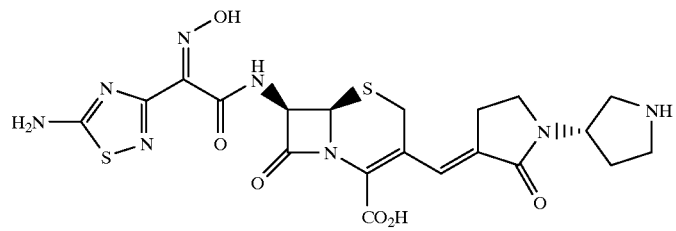

C: (6R,7R)-7-[(Z)-2-(5-Amino-[1,2,4]thiadiazol-3-yl)-2-hydroxyimino-acetylamino]-3-[(E)-(R)-1'-iminomethyl-2-oxo-[1,3']bipyrrolidinyl-3-ylidenemethyl]-8-oxo-5-thia-1-aza-bicyclo[4.2.0]oct-2-ene-2-carboxylic acid

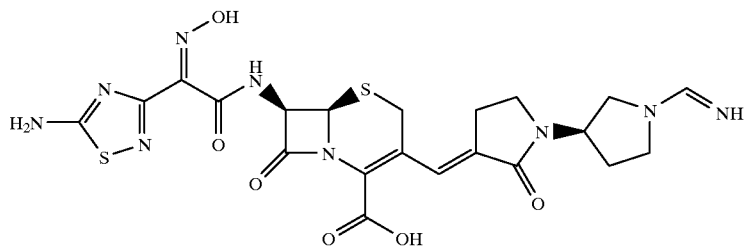

D: (6R, 7R)-7-[(Z)-2-(5-Amino-[1,2,4]thiadiazol-3-yl)-2-hydroxyimino-acetylamino]-3-[(E)-((R)-1'-carbamimidoyl-2-oxo-[1,3']bipyrrolidinyl-3-ylidenemethyl)]-8-oxo-5-thia-1-aza-bicyclo[4.2.0]oct-2-ene-2-carboxylic acid

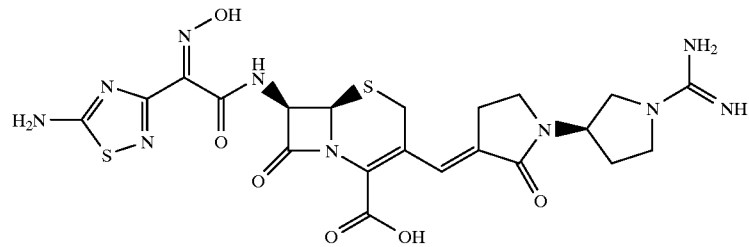

E: (6R, 7R)-7-[(Z)-2-(5-Amino-[1,2,4]thiadiazol-3-yl)-2-hydroxyimino-acetylamino]-3-[(E)-1-azetidin-3-ylmethyl-2-oxo-pyrrolidin-3-ylidenemethyl]-8-oxo-5-thia-1-aza-bicyclo[4.2.0]oct-2-ene-2-carboxylic acid

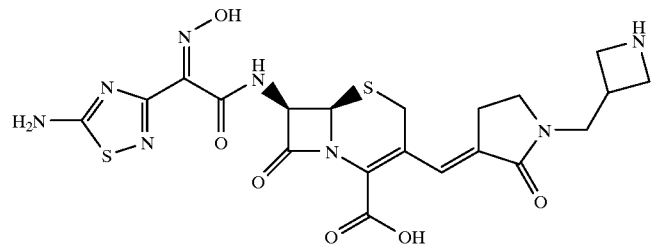

F: (6R, 7R)-7-[(Z)-2-(5-Amino-[1,2,4]thiadiazol-3-yl)-2-hydroxyimino-acetylamino]-3-[(E)-5'-hydroxymethyl-2-oxo-[1,3']bipyrrolidinyl-3-ylidenemethyl]-8-oxo-5-thia-1-aza-bicyclo[4.2.0]oct-2-ene-2-carboxylic acid

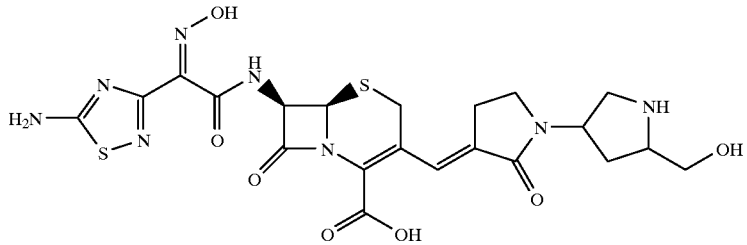

The compounds of formula I as well as their salts and readily hydrolyzable esters can be hydrated. The hydration can be effected in the course of the making the hydrate or can occur gradually as a result of hygroscopic properties of an initially anhydrous product.

The compounds of the present invention are useful as antibiotics having potent and broad antibacterial activity; especially against methicillin resistent *Staphylococci aureus* (MRSA) and *Pseudomonas aeruginosa*.

The products in accordance with the invention can be used as medicaments, for example, in the form of pharmaceutical preparations for parenteral administration, and for this purpose are preferably made into preparations as lyophilisates or dry powders for dilution with customary agents, such as water or isotonic common salt or carbohydrate (e.g. glucose) solution.

Depending on the nature of the pharmacologically active compound the pharmaceutical preparations can contain the compound for the prevention and treatment of infectious diseases in mammals, human and non-human. A daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

Representative compounds (A and B, above) of the present invention were tested. In vitro activity was determined by minimum inhibitory concentration by the agar dilution method in Mueller Hinton agar, inoculum=$10^4$ CFU/spot.

| In vitro activity (MIC [μg/ml]) | | |
|---|---|---|
| | A | B |
| MIC *S.aureus* 6538 (MSSA) | 0.5 | 0.25 |
| MIC *S. aureus* 743 (MRSA) | 2 | 2 |
| MIC *S. aureus* 270A (MRSA) | 2 | 4 |
| MIC90 (MRSA, n = 38)* | 4 | 4 |
| MIC *P. aeruginosa* ATCC27853 | 2 | 4 |

*Agar dilution method on Mueller-Hinton agar, inoculum: $10^5$ CFU/spot

In vivo efficacy was determined with a sc abscess model in mice, infected with *S. aureus* 270 A (MRSA). The dose (ip) was 10 mg/kg. The median log of colony forming units (CFU) was determined. A more than hundred-fold reduction in the number of CFUs was achieved by compound A as compared to the untreated control. The compound A was more active than vancomycin, the standard drug for clinical infections due to MRSA.

| In vivo efficacy | | |
|---|---|---|
| Compound | no. mice | Median log CFU |
| None | 3 | 6.92 |
| Vancomycin | 3 | 5.28 |
| A | 3 | 4.72 |

The compounds of the formula I in accordance with the invention as well as their pharmaceutical acceptable salts, hydrates, or readily hydrolyzable esters can be made in accordance with the invention for example by (a) treating a compound having the formula II

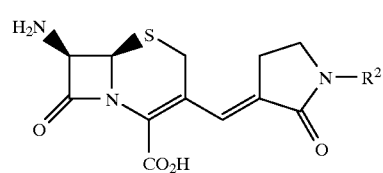

II wherein $R^2$ is defined as above, or an ester or a salt thereof, the amino group and the carboxylic groups present in the compound of formula II may be unprotected or protected, with a carboxylic acid of formula III

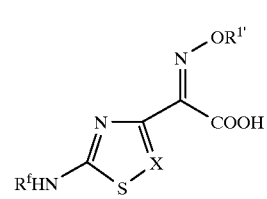

III in which $R^f$ is hydrogen or an amino protecting group, $R^1$ is hydrogen, cyclopentyl or a hydroxy protecting group and X is as defined above, or with a reactive functional derivative thereof, or (b) cleaving off the amino, hydroxy and/or carboxy protecting group in a compound having the formula IV

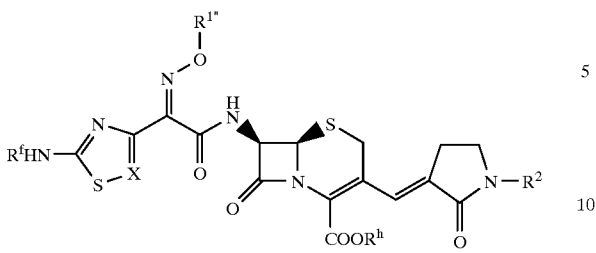

IV in which $R^2$ is as defined above, $R^f$ is hydrogen or an amino protecting group, $R^{1'''}$ is hydrogen or a hydroxy protecting group, $R^h$ is hydrogen or a carboxy protecting group, provided that at least one of $R^f$, $R^{1'''}$ and $R^h$ is a corresponding protecting group, or a salt thereof.

The reaction of compounds of formula II and III or a reactive derivative of formula III according to embodiment (a) can be carried out in a manner known per se. The carboxy group in compounds of formula II can be protected, for example, by esterification to form a readily cleavable ester such as a silyl ester (e.g. the trimethylsilyl ester), a tert-butyl, allyl, p-methoxybenzyl or a benzhydryl ester.

The amino group present in the acylating agent of formula III can be protected. Possible protecting groups $R^f$ are, for example, protecting groups which are cleavable by acid hydrolysis (e.g. the tertbutoxycarbonyl or trityl groups), by basic hydrolysis (e.g. the trifluoroacetyl group), by hydrazinolysis (e.g. the phthalimido group) or by catalytic cleavage in presence of Pd (the allyloxycarbonyl group). Preferred protecting groups are the allyloxycarbonyl, the tert-butyloxy-carbonyl, the chloroacetyl, bromoacetyl and iodoacetyl groups, especially the chloroacetyl group. These last-mentioned protecting groups can be cleaved off by treatment with thiourea. The 7-amino group in compounds II can be protected, for example, by a silyl protective group such as the trimethylsilyl group.

In reacting a 7-amino compound of formula II with a carboxylic acid of formula III or a reactive functional derivative thereof, for example, a free carboxylic acid can be reacted with an aforementioned ester of a compound of formula II in the presence of a carbodiimide such as dicyclohexylcarbodiimide in an inert solvent such as ethyl acetate, acetonitrile, dioxane, chloroform, methylene chloride, benzene or dimethylformamide, and subsequently the ester group can be cleaved off.

According to another embodiment, a salt of an acid of formula II (e.g. a trialkylammonium salt such as the triethylammonium salt) is reacted with a reactive functional derivative of a carboxylic acid of formula III in an inert solvent (e.g. dimethylformamide or dimethylacetamide).

According to a further embodiment, preferred acylation, where the amino group present in the acylating agent of formula III need not be protected, involves the use of a reactive functional derivative of the acylation agent of formula III, for example, a mixed anhydride of thiophosphoric acid of the carboxylic acid, a 1-hydroxybenzotriazole ester or a 2-benzothiazolyl thioester. For instance, a mixed anhydride of thiophosphoric acid may be reacted with the compound of formula II preferably in a polar solvent as dimethyl formamide (DMF), dichloromethane, or a mixture of DMF/i-propanol/water in presence of a base as e.g. triethylamine. The 1-hydroxybenzotriazole ester as well as the 2-benzothiazolyl thioester may be reacted with the compound II in an inert organic solvent such as a chlorinated hydrocarbon e.g. methylene chloride, or in dimethylformamide, dimethylacetamide, acetone, ethyl acetate or in a mixture of such solvents with water. Such a reactive 2-benzthiazolyl thioester is for example

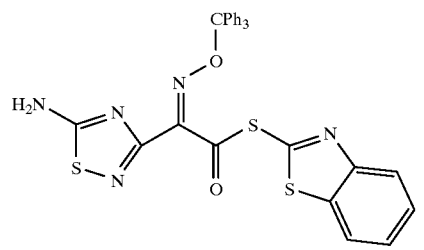

IIIa this compound is new and is part of the present invention.

The reaction of a 7-amino compound of formula II with the carboxylic acid of formula III or a reactive derivative thereof can conveniently be carried out at a temperature between about −40° C. and +60° C., e.g. at room temperature.

Embodiment (b) of the process of the present invention involves deprotection (removal) of a protected amino group in the 2-position of the thiazol or the thiadiazol ring and/or the protected pyrrolidin ring ($R^4$ as the protecting group), and/or protected hydroxy or carboxylic groups present in a compound of formula IV and can be carried and as follows:

Removal of Amino Protecting Groups

As mentioned above the amino protecting groups may be cleaved off by acid hydrolysis (e.g. the tert-butoxycarbonyl or trityl group), e.g. aqueous formic acid, trifluoroacetic acid or by basic hydrolysis (e.g. the trifluoroacetyl group). Further protecting groups may be cleaved off by hydrazinolysis (e.g. the phthalimido group). The allyloxycarbonyl group may be cleaved off by Pd catalyzed transfer to nucleophiles. The chloroacetyl, bromoacetyl and iodoacetyl groups are cleaved off by treatment with thiourea.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about −30° C. to +40° C.). Protecting groups which are cleavable under basic conditions are generally hydrolyzed with dilute aqueous caustic alkali at 0° C. to 30° C. The chloroacetyl, bromoacetyl and iodoacetyl protecting groups can be cleaved off using thiourea in acidic, neutral or alkaline medium at about 0° C.–30° C.

Removal of Hydroxy Protecting Groups

The term "hydroxy protecting group" refers to protecting groups as conventionally used in the art such as trityl (triphenylmethyl), trimethylsilyl, tert.-butyl-dimethylsilyl, dimethylphenylsilyl, triphenylmethyl, lower alkanoyl, acetyl, tetrahydropyranyl, benzyl, p-nitrobenzyl and the like.

Preferred hydroxy protecting groups are such as are commonly known in the art, e.g. for protection of hydroxyimino groups ($R^1$=hydrogen in compounds of formula I), usually trityl, lower alkanoyl, especially acetyl, tetrahydropyranyl.

These protecting groups are e.g. removed as follows:

| | |
|---|---|
| -trityl | in acidic solvents like 90% formic acid at about 0 to 50° C. or triethylsilane in trifluoroacetic acid at about −20 to 25° C.; in organic solutions of hydrochloric acid at about −50 to 25° C.; |
| -acetyl | with weak inorganic bases like sodium bicarbonate in methanol or ethanol/water at about 0 to 50° C.; |
| -tetrahydropyranyl | with weak organic acids like p-toluenesulfonic acid in an alcohol, e.g. ethanol, at about 0° C. to the boiling point of the mixture. |

Removal of Protecting Groups at the Carboxy Function

The term "carboxylic acid protecting group" refers to protecting groups conventionally used to replace the acidic proton of a carboxylic acid. As carboxyl protecting groups one may utilize an ester form which can be easily converted into a free carboxyl group under mild conditions, for example, methoxymethyl, methylthiomethyl, 2,2,2-trichloroethyl, 2-haloethyl, 2-(trimethylsilyl)ethyl, tert-butyl, allyl, benzyl, triphenylmethyl (trityl), diphenylmethyl, p-nitrobenzyl, p-methoxybenzyl, trimethylsilyl, triethylsilyl, tert-butyldimethylsilyl, i-propyl-dimethylsilyl. Preferred are benzhydryl, tert-butyl, p-nitrobenzyl, p-methoxybenzyl and allyl.

These protecting groups may be removed as follows:

| | |
|---|---|
| benzhydryl | trifluoroacetic acid with anisol, phenol, cresol or triethylsilane at about −40° C. to room temperature; hydrogen with Pd/C in an alcohol such as ethanol or in tetrahydrofuran; BF₃-etherate in acetic acid at about 0 to 50° C.; |
| tert-butyl | formic acid or trifluoroacetic acid with or without anisol, phenol, cresol or triethylsilane and a solvent such as dichloromethane at about −10° C. to room temperature; |
| p-nitrobenzyl | sodium sulfide in acetone/water at about 0 to room temperature; or hydrogen with Pd/C in an alcohol such as ethanol or in tetrahydrofuran; |
| p-methoxybenzyl | formic acid at about 0 to 50° C.; or trifluoroacetic acid and anisol, phenol or triethylsilane at about −40° C. to room temperature; |
| allyl | palladium(O) catalyzed transalkylation reaction in the presence of tri-n-butyltinhydride and acetic acid, see for example F. Guibe et al. in J. Org. Chem. (1987) 52, 4984–4993 |

Further methods for making the compounds according to the invention are known in the art. Compounds of formula I can for example be made in analogy to the methods described in U.S. Pat. No. 5,523,400 and according to the examples given below.

EXAMPLES

Example 1

Preparation of the acylation agent (Z)-(5-Amino-[1,2,4] thiadiazol-3-yl)-trityloxyimino-thioacetic acid S-benzothiazol-2-yl ester

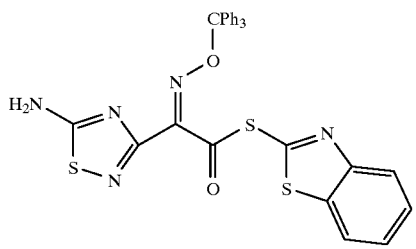

To a suspension of (Z)-(5-amino-[1,2,4]thiadiazol-3-yl)-trityloxyimino-acetate 1-allyl-1-methyl-pyrrolidinium salt (1.89 g, 3.4 mmol) in 25 ml acetonitrile were added at 0° C. 2,2'-dithio-bisbenzothiazole (1.36 g, 4.1 mmol). A solution of triethylphosphite (0.7 ml, 5.8 mmol) in 7 ml acetonitirile was added within 40 min. and the mixture was stirred at room temperature for 27 h. The precipitate was collected by filtration and washed with acetonitrile and n-hexane.

Yield: 1.615 g (82%) beige crystals; IR(IKBr) 1704, 1619, 1003 cm⁻¹; MS(ISP) 580.2 (M+H)⁺.

Example 2

2.1. Preparation of a mixture of (1R, 3'R)- and (1S, 3'R)-3-bromo-2-oxo-[1,3']bipyrrolidinyl-1'-carboxylic acid allyl ester

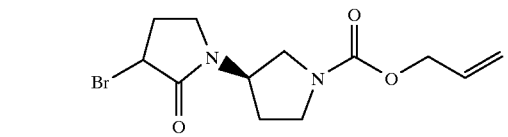

A solution of (R)-3-amino-pyrrolidine-1-carboxylic acid allyl ester trifluoroacetate (1:3.2) (47.84 g, 0.089 mol) in 180 ml dichloromethane was treated with 50% aqueous sodium hydroxide solution (72 ml, 0.894 mol). To the vigorously stirred mixture was added within 18 min. at 0° C. a solution of 2-bromo-4-chloro-butanoyl chloride (21.62 g, 0.098 mol) in 90 ml dichloromethane. The reaction mixture was stirred at 0° C. for 1 h. The phases were separated, the aqueous phase was extracted twice with 100 ml dichloromethane and the combined organic phases were washed twice with 50 ml water. They were dried over magnesium sulfate and the solvent was removed by evaporation. The residual yellow oil (32 g) was redissolved in 380 ml dichloromethane and 190 ml of a 50% aqueous sodium hydroxide solution and 3.23 g Dowex 2×10 were added with vigorous stirring at room temperature. After 6 h, the phases were separated, the aqueous phase was extracted twice with 150 ml dichloromethane. The combined organic phases were washed once with 100 ml water, once with brine, were dried over magnesium sulfate and concentrated.

Yield: 28.7 g (quant.) of a yellow oil; IR(neat) 1697cm⁻¹; MS(ISP) 317.2 (M)⁺.

According to the procedure set forth in the preceding example, the following additional compounds were prepared:

2.2. Mixture of (1R,3'S) and (1S,3'S)-3-bromo-2-oxo-[1,3'] bipyrrolidinyl-1'-carboxylic acid allyl ester IR(neat) 1697 cm⁻¹; MS(ISP) 317.1 (M)⁺.

2.3. Mixture of (3RS,3'RS)- and (3RS,3'SR)-3-bromo-2-oxo-[1,3']bipyrrolidinyl-1'-carboxylic acid allyl ester IR(neat) 1695 cm⁻¹; MS(EI) 259 (M-OC3H5).

2.4. (RS)-3-(3-Bromo-2-oxo-pyrrolidin-1-yl)-azetidine-1-carboxylic acid allyl ester IR(neat) 1700 cm$^{-1}$; MS(ISP) 303.2 (M)$^+$.

2.5. (RS)-4-(3-Bromo-2-oxo-pyrrolidin-1-ylmethyl)-piperidine-1-carboxylic acid allylester IR(neat) 1699 cm$^{-1}$; MS(ISP) 345.2 (M)$^+$.

2.6. (RS)-4-(3-Bromo-2-oxo-pyrrolidin-1-yl)-pyrazolidine-1,2-dicarboxylic acid diallyl ester IR(KBr) 1704 cm$^{-1}$; MS(ISP) 404 (M+H)$^+$.

2.7. 1:1 Mixture of (3S,4R)-3-[(R)- and -[(S)-3-bromo-2-oxo-pyrrolidin-1-ylmethyl]-4-trifluoromethyl-pyrrolidine-1-carboxylic acid allyl ester IR(KBr) 1702 cm$^{-1}$; MS(ISP) 401.3 (M+H)$^+$.

2.8. Mixture of (3R,3'S,5'S)- and (3S,3'S,5'S)-3-bromo-5'-dimethylcarbamoyl-2-oxo-[1,3']bipyrrolidinyl-1'-carboxylic acid allyl ester IR(KBr) 1699, 1649 cm$^{-1}$; MS(EI) 388 (M+H)$^+$.

2.9. 1:1 Mixture of (3R,3'S,5'R)- and (3S,3'S,5R)-3-bromo-5'-dimethylcarbamoyl-2-oxo-[1,3]bipyrrolidinyl-1'-carboxylic acid allyl ester IR(KBr) 1698, 1654 cm$^{-1}$; MS(ISP) 388.1 (M+H)$^+$.

2.10. (RS)-3-(3-Bromo-2-oxo-pyrrolidin-1-ylmethyl)-azetidine-1-carboxylic acid allyl ester IR(KBr) 1698 cm$^{-1}$; MS(ISP) 319.2 (M+H)$^+$.

Example 3

3.1. Mixture of (1R,3'R) and (1S,3'R)-(1'-allyloxycarbonyl-2-oxo-[1,3']bipyrrolidinyl-3-yl)-triphenyl-phosphonium bromide

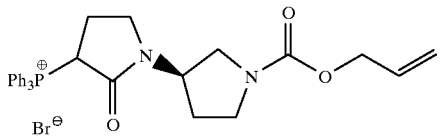

Triphenylphosphine (23.62 g, 0.090 mol) and a mixture of (1R,3'R)- and (1S,3'R)-3-bromo-2-oxo-[1,3']bipyrrolidinyl-1'-carboxylic acid allyl ester (28.56 g, 0.090 mol) were dissolved in 80 ml dichloromethane. The solvent was removed in vacuo and the residual oil was heated for 2 h at 100° C. The resulting solid was dissolved in 130 ml dichloromethane and added with stirring to 1500 ml n-hexane resulting in the separation of the product. The solvent was decanted and the residue triturated with 1500 ml diethylether. The thereby formed solid was collected by filtration, washed with n-hexane and diethylether and dried in vacuo, yielding 45.1 g (78%) of the product as colorless crystals.

IR(KBr) 1682 cm$^{-1}$; MS(ISP) 499.3 (M)$^+$.

According to the procedure set forth in the preceding example, the following additional compounds were prepared:

3.2. Mixture of (3R,3'S) and (3S,3'S)-(1'-allyloxycarbonyl-2-oxo-[1,3']bipyrrolidinyl-3-yl)-triphenyl-phosphonium bromide IR(KBr) 1684 cm$^{-1}$; MS(ISP) 499.2 (M)$^+$.

3.3. Mixture of (3RS,3'RS)- and (3RS,3'SR)-(1'-allyloxycarbonyl-2-oxo-[1,3']bipyrrolidinyl-3-yl)-triphenyl-phosphonium bromide IR(KBr) 1684 cm$^{-1}$; MS(ISP) 499.4 (M+H)$^+$.

3.4. (RS)-[1-(1-Allyloxycarbonyl-azetidin-3-yl)-2-oxo-pyrrolidin-3-yl]-triphenyl-phosphonium bromide IR(KBr) 1687 cm$^{-1}$; MS(ISP) 485.4 (M+H)$^+$.

3.5. (RS)-[1-(1-Allyloxycarbonyl-piperidin-4-ylmethyl)-2-oxo-pyrrolidin-3-yl]-triphenyl-phosphonium bromide IR(KBr) 1688 cm$^{-1}$; MS(ISP) 527.3 (M)$^+$.

3.6. (RS)-[1-(1,2-Bis-allyloxycarbonyl-pyrazolidin-4-yl)-2-oxo-pyrrolidin-3-yl]-triphenyl-phosphonium bromide IR(KBr) 1688 cm$^{-1}$; MS(ISP) 585.5 (H)$^+$.

3.7. 1:1 Mixture of [(R)- and [(S)-1-[(S)-1-allyloxycarbonyl-pyrrolidin-2-ylmethyl]-2-oxo-pyrrolidin-3-yl]-triphenyl-phosphonium bromide IR(KBr) 1682 cm$^{-1}$; MS(ISP) 513.4 (M)$^+$.

3.8. 1:1 Mixture of (3S,4R)-[(R)- and -[(S)-1-(1-allyloxycarbonyl-4-trifluoromethyl-pyrrolidin-3-ylmethyl)-2-oxo-pyrrolidin-3-yl]-triphenyl-phosphonium bromide IR(KBr) 1690 cm$^{-1}$; MS(ISP) 581.2 (M+H)$^+$.

3.9. 1:1 Mixture of (3R,3'S,5'S)- and (3S,3'S,5'S)-(1'-allyloxycarbonyl-5'-dimethylcarbamoyl-2-oxo-[1,3'] bipyrrolidinyl-3-yl)-triphenyl-phosphonium bromide IR(KBr) 1687 cm$^{-1}$; MS(ISP) 570.3 (M)$^+$.

3.10. 1:1 Mixture of (3R,3'S,5'R)- and (3S,3'R,5'S)-3-(1'-allyloxycarbonyl-5'-dimethylcarbamoyl-2-oxo-[1,3'] bipyrrolidinyl-3-yl)-triphenyl-phosphonium bromide IR(KBr) 1686 cm$^{-1}$; MS(ISP) 570.3 (M)$^+$.

3.11. (RS)-[1-(1-Allyloxycarbonyl-azetidin-3-ylmethyl)-2-oxo-pyrrolidin-3-yl]-triphenyl-phosphonium bromide (1:1)

IR(KBr) 1679 cm$^{-1}$; MS(ISP) 499.2 (M)$^+$.

Example 4

4.1. (E)-(2R,6R,7R)-3-[(R)-1'-Allyloxycarbonyl-2-oxo-[1,3']bipyrrolidinyl-3-ylidenemethyl]-7-tert-butoxycarbonylamino-8-oxo-5-thia-1-aza-bicyclo[4.2.0]oct-3-ene-2-carboxylic acid benzhydryl ester

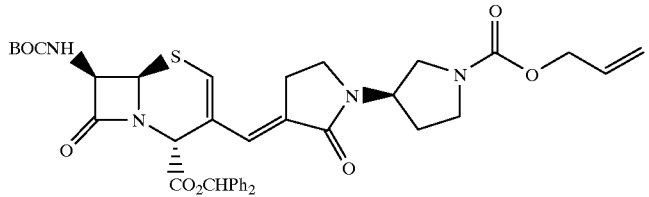

A suspension of the mixture of (1R,3'R) and (1S,3'R)-(1'-allyloxycarbonyl-2-oxo-[1,3']bipyrrolidinyl-3-yl)-triphenyl-phosphonium bromide (43.5 g, 0.075 mol) and (2R,6R,7R)-tert-butoxycarbonylamino-3-formyl-8-oxo-5-thia-1-aza-bicyclo[4.2.0]oct-3-ene-2-carboxylic acid benzhydryl ester (33.74 g, 0.068 mol) in 950 ml butylenoxide was refluxed for 1.5 h. The solvent was removed in vacuo and the residue was purified by column chromatography (300 g SiO2, ethyl acetate: n-hexane=2:1, 3:1) giving 67.8 g of a 1:1 (molar ratio) mixture containing the product and triphenylphosphine oxide as a yellow foam. Further purification was not necessary to proceed with the next step.

IR(KBr) 1781, 1744 cm$^{-1}$; MS(ISP) 732.5 (M+NH$_4$)$^+$.

According to the procedure set forth in the preceding example, the following additional compounds were prepared:

4.2. (E)-(2R,6R,7R)-3-[(S)-1'-Allyloxycarbonyl-2-oxo-[1,3']bipyrrolidinyl-3-ylidenemethyl]-7-tert-butoxycarbonylamino-8-oxo-5-thia-1-aza-bicyclo[4.2.0]oct-3-ene-2-carboxylic acid benzhydryl ester IR(KBr) 1782, 1744, 1705 cm$^{-1}$; MS(ISP) 732.4 (M+NH$_4$)$^+$.

4.3. Mixture of (E)-(2R,6R,7R)-3-[(R)- and -[(S)-1'-allyloxycarbonyl-2-oxo-[1,3']bipyrrolidinyl-3-ylidenemethyl]-7-tert-butoxycarbonylamino-8-oxo-5-thia-1-aza-bicyclo[4.2.0]oct-3-ene-2-carboxylic acid benzhydryl ester IR(KBr) 1780, 1744, 1704 cm$^{-1}$; MS(ISP) 715.4 (M+H)$^+$.

4.4. (E)-(2R,6R,7R)-3-[1-(1-Allyloxycarbonyl-azetidin-3-yl)-2-oxo-pyrrolidin-3-ylidenemethyl]-7-tert-butoxycarbonylamino-8-oxo-5-thia-1-aza-bicyclo[4.2.0]oct-3-ene-2-carboxylic acid benzhydryl ester IR(KBr) 1782, 1743, 1713 cm$^{-1}$; MS(ISP) 718.4 (M+NH$_4$)$^+$.

4.5. (E)-(2R,6R,7R)-3-[1-(1-Allyloxycarbonyl-piperidin-4-ylmethyl)-2-oxo-pyrrolidin-3-ylidenemethyl]-7-tert-butoxycarbonylamino-8-oxo-5-thia-1-aza-bicyclo[4.2.0]oct-3-ene-2-carboxylic acid benzhydryl ester IR(KBr) 1779, 1743, 1692 cm$^{-1}$; MS(ISP) 760.5 (M+NH$_4$)$^+$.

4.6. (E)-(2R,6R,7R)-3-[1-[(3S,4R)-1-Allyloxycarbonyl-4-trifluoromethylpyrrolidin-3-ylmethyl]-2-oxo-pyrrolidin-3-ylidenemethyl]-7-tert-butoxycarbonylamino-8-oxo-5-thia-1-aza-bicyclo[4.2.0]oct-3-ene-2-carboxylic acid benzhydryl ester IR(KBr) 1782, 1711 cm$^{-1}$; MS(ISP) 797.0 (M+H)$^+$.

Example 5

5.1. 1:1 Mixture of (E)-(5R,6R,7R)- and-(5S,6R,7R)-3-[(R)-1'-allyloxycarbonyl-2-oxo-[1,3']bipyrrolidinyl-3-ylidenemethyl]-7-tert-butoxycarbonylamino-5,8-dioxo-5-thia-1-aza-bicyclo[4.2.0]oct-2-ene-2-carboxylic acid benzhydryl ester magnesium sulfate, concentrated after filtration and purified by column chromatography (1000 g SiO$_2$, ethyl acetate: n-hexane=3: 1, 1:0 and ethyl acetate:methanol=9: 1).

Yield: 36.3 (73%);

IR(KBr) 1797, 1711 cm$^{-1}$; MS(ISP) 748.5 (M+NH$^4$)$^+$.

According to the procedure set forth in the preceding example, the following additional compounds were prepared:

5.2. Mixture of (E)-(5R,6R,7R)- and-(5S,6R,7R)-3-[(S)-1'-allyloxycarbonyl-2-oxo-[1,3']bipyrrolidinyl-3-ylidenemethyl]-7-tert-butoxycarbonylamino-5,8-dioxo-5-thia-1-aza-bicyclo[4.2.0]oct-2-ene-2-carboxylic acid benzhydryl ester IR(KBr) 1796, 1710 cm$^{-1}$; MS(ISP) 748.5 (M+NH$_4$)$^+$.

5.3. Mixture of (E)-(5R,6R,7R)- and -(5S,6R,7R)-3-(1'-allyloxycarbonyl-2-oxo-[1,3']bipyrrolidinyl-3-ylidenemethyl)-7-tert-butoxycarbonylamino-5,8-dioxo-5-thia-1-aza-bicyclo[4.2.0]oct-2-ene-2-carboxylic acid benzhydryl ester (config. at C3' in bipyrrolidine-moiety R and S)

IR(KBr) 1796, 1716 cm$^{-1}$; MS(ISP) 748.5 (M+NH$_4$)$^+$.

5.4. Mixture of (E)-(5R,6R,7R)- and -(5S,6R,7R)-3-[1-(1-allyloxycarbonyl-azetidin-3-yl)-2-oxo-pyrrolidin-3-ylidenemethyl]- 7-tert-butoxycarbonylamino-5,8-dioxo-5-thia-1-aza-bicyclo[4.2.0]oct-2-ene-2-carboxylic acid benzhydryl ester IR(KBr) 1797, 1718 cm$^{-1}$; MS(ISP) 734.5 (M+NH$_4$)$^+$.

5.5. 1:1 Mixture of (E)-(5R,6R,7R)-and (5S,6R,7R)-3-[1-(1-allyloxycarbonyl-piperidin-4-ylmethyl)-2-oxo-pyrrolidin-3-ylidenemethyl]-7-tert-butoxycarbonylamino-5,8-dioxo-5-thia-1-aza-bicyclo[4.2.0]oct-2-ene-2-carboxylic acid benzhydryl ester IR(KBr) 1795, 1721, 1692 cm$^{-1}$; MS(ISP) 776.5 (M+NH$_4$)$^+$.

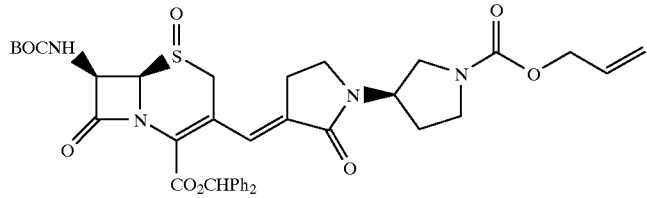

A solution of the mixture described above of (E)-(2R,6R,7R)-3-[(R)-1'-allyloxycarbonyl-2-oxo-[1,3']bipyrrolidinyl-3-ylidenemethyl]-7-tert-butoxycarbonylamino-8-oxo-5-thia-1-aza-bicyclo[4.2.0]oct-3-ene-2-carboxylic acid benzhydryl ester and triphenylphosphine oxide (67.8 g, 0.068 mol) in 400 ml dichloromethane was cooled to −10° C. To this was added dropwise a solution of m-chloroperbenzoic acid (70%, 16.82 g, 0.068 mol) in 250 ml dichloromethane. The resulting solution was stirred for 2.5 h at −5 to 0° C., 150 ml aqueous sodium thiosulfate solution (5%) was added and the mixture was stirred for 15 min. The phases were separated and the aqueous phase was extracted twice with 100 ml dichloromethane. The combined organic phase were washed with each 150 ml of aqueous solutions of sodium thiosulfate (5%), sodium bicarbonate (5%) and finally brine. The solution was dried over 5.6. Mixture of (E)-(5R,6R,7R)- and -(5S,6R,7R)-3-[1-[(3S,4R)-1-Allyloxycarbonyl-4-trifluoromethyl-pyrrolidin-3-ylmethyl]-2-oxo-pyrrolidin-3-ylidenemethyl]-7-tert-butoxycarbonylamino-5,8-dioxo-5-thia-1-aza-bicyclo[4.2.0]oct-2-ene-2-carboxylic acid benzhydryl ester IR(KBr) 1796, 1716 cm$^{-1}$; MS(ISP) 813.4 (M+H)$^+$.

Example 6

6.1. (E)-(6R,7R)-3-[(R)-1'-Allyloxycarbonyl-2-oxo-[1,3']bipyrrolidinyl-3-ylidenemethyl]-7-tert-butoxycarbonylamino-8-oxo-5-thia-1-aza-bicyclo[4.2.0]oct-2-ene-2-carboxylic acid benzhydryl ester

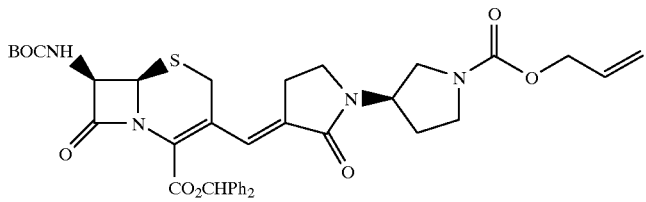

To a solution of a mixture of a 1:1 mixture of (E)-(5R,6R, 7R)- and-(5S,6R,7R)-3-[(R)-1'-allyloxycarbonyl-2-oxo-[1, 3']bipyrrolidinyl-3-ylidenemethyl]-7-tertbutoxycarbonylamino-5,8-dioxo-5-thia-1-aza-bicyclo[4.2.0]oct-2-ene-2-carboxylic acid benzhydryl ester (36.3 g, 0.050 mol) in 370 ml dichloromethane, 30 ml DMF and 44 ml N-methylacetamide was added within 20 min. at –30° C. a solution of phosphorous tribromide (19.1 ml, 0.203 mol) in 56 ml dichloromethane. After stirring for 1.5 h at –30° C., the mixture was allowed to warm up to –5° C. and quenched with 800 ml cold water. The phases were separated, the aqueous phase was extracted twice with 300 ml dichloromethane. The combined organic phases were washed with 500 ml water and brine and dried over magnesium sulfate. After removal of the solvent in vacuo, the residue was treated with a 1:1 mixture of ethyl acetate and n-hexane (700 ml). The precipitated product was collected by filtration.

Yield: 32.9 g (91%) orange crystals.

IR(KBr) 1785, 1715 cm$^{-1}$; MS(ISP) 732.5 (M+NH$_4$)$^+$.

According to the procedure set forth in the preceding example, the following additional compounds were prepared:

6.2. (E)-(6R,7R)-3-[(S)-1'-Allyloxycarbonyl-2-oxo-[1,3'] bipyrrolidinyl-3-ylidenemethyl]-7-tert-butoxycarbonylamino-8-oxo-5-thia-1-aza-bicyclo[4.2.0] oct-2-ene-2-carboxylic acid benzhydryl ester IR(KBr) 1786, 1712 cm$^{-1}$; MS(ISP) 732.5 (M+NH$_4$)$^+$.

6.3. Mixture of (E)-(6R,7R)-3-[(R)- and -[(S)-1'-allyloxycarbonyl-2-oxo- [1,3']-bipyrrolidinyl-3-ylidenemethyl]-7-tert-butoxycarbonylamino-8-oxo-5-thia-1-aza-bicyclo[4.2.0]oct-2-ene-2-carboxylic acid benzhydryl ester IR(KBr) 1785, 1712 cm$^{-1}$; MS(ISP) 732.6 (M+NH$_4$)$^+$.

6.4. (E)-(6R,7R)-3-[1-(1-Allyloxycarbonyl-azetidin-3-yl)-2-oxo-pyrrolidin-3-ylidenemethyl]-7-tert-butoxycarbonylamino-8-oxo-5-thia-1-aza-bicyclo[4.2.0] oct-2-ene-2-carboxylic acid benzhydryl ester IR(KBr) 1786, 1717 cm$^{-1}$; MS(ISP) 718.6 (M+NH$_4$)$^+$.

6.5. (E)-(6R,7R)-3-[1-(1-Allyloxycarbonyl-piperidin-4-ylmethyl)-2-oxo-pyrrolidin-3-ylidenemethyl]-7-tert-butoxycarbonylamino-8-oxo-5-thia-1-aza-bicyclo[4.2.0] oct-2-ene-2-carboxylic acid benzhydryl ester IR(KBr) 1784, 1688 cm$^{-1}$; MS(ISP) 760.6 (M+NH$_4$)$^+$.

6.6. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin 1-yl]-pyrazolidine-1,2-dicarboxylic acid diallyl ester IR(KBr) 1785 cm$^{-1}$; MS(ISP) 800.6 (M+H)$^+$.

6.7. (E)-(6R,7R)-3-[1-[(S)-1-Allyloxycarbonyl-pyrrolidin-ylmethyl]-2-oxo-pyrrolidin-3-ylidenemethyl]-7-tert-butoxycarbonylamino-8-oxo-5-thia-1-aza-bicyclo[4.2.0] oct-2-ene-2-carboxylic acid benzhydryl ester IR(KBr) 1784 cm$^{-1}$; MS(ISP) 729.3 (M+H)$^+$.

6.8. (E)-(6R,7R)-3-[1-[(3S,4R)-1-Allyloxycarbonyl-4-trifluoromethyl-pyrrolidin-3-ylmethyl]-2-oxo-pyrrolidin-3-ylidenemethyl]-7-tert-butoxycarbonylamino-8-oxo-5-thia-1-aza-bicyclo[4.2.0]oct-2-ene-2-carboxylic acid benzhydryl ester IR(KBr) 1790, 1713 cm$^{-1}$; MS(ISP) 797.4 (M+H)$^+$.

6.9. (E)-(6R,7R)-3-[(3'S,5'S)-1'-Allyloxycarbonyl-5'-dimethylcarbamoyl-2-oxo-[1,3']bipyrrolidinyl-3-ylidenemethyl]-7-tert-butoxycarbonylamino-8-oxo-5-thia-1-aza-bicyclo[4.2.0]oct-2-ene-2-carboxylic acid benzhydryl ester IR(KBr) 1787, 1713 cm$^{-1}$; MS(ISP) 786.4 (M+H)$^+$.

6.10. (E)-(6R,7R)-3-[(3'S,5'R)-1'-Allyloxycarbonyl-5'-dimethylcarbamoyl-2-oxo-[1,3 ']bipyrrolidinyl-3-ylidenemethyl]-7-tert-butoxycarbonylamino-8-oxo-5-thia-1-aza-bicyclo[4.2.0]oct-2-ene-2-carboxylic acid benzhydryl ester IR(KCr) 1786, 1712 cm$^{-1}$; MS(ISP) 786.5 (M+H)$^+$.

6.11. (E)-(6R,7R)-3-[1-(1-Allyloxycarbonyl-azetidin-3-ylmethyl)-2-oxo-pyrrolidin-3-ylidenemethyl]-7-tert-butoxycarbonylamino-8-oxo-5-thia-1-aza-bicyclo[4.2.0] oct-2-ene-2-carboxylic acid benzhydryl ester IR(KBr) 1780, 1700 cm$^{-1}$; MS(ISP) 715.3 (M+H)$^+$.

Example 7

7.1. (E)-(6R,7R)-3-[(R)-1'-Allyloxycarbonyl-2-oxo-[1,3'] bipyrrolidinyl-3-ylidenemethy)-7-amino-8-oxo-5-thia-1-aza-bicyclo[4.2.0]oct-2-ene-2-carboxylic acid trifluoroacetate

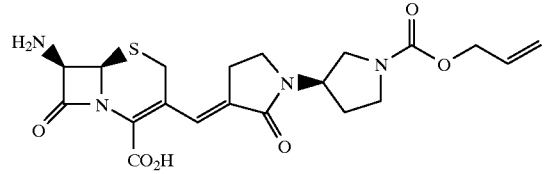

To a solution of (E)-(6R,7R)-3-[(R)-1'-allyloxycarbonyl-2-oxo-[1,3']bipyrrolidinyl-3-ylidenemethyl]-7-tert-butoxycarbonylamino-8-oxo-5-thia-1-aza-bicyclo[4.2.0] oct-2-ene-2-carboxylic acid benzhydryl ester (32.9 g, 0.046 mol) in 320 ml dichloromethane was added at 0° C. 32 ml anisol and 180 ml trifluoroacetic acid. The mixture was stirred for 2.5 h stirring at room temperature, concentrated to a volume of 50 ml and poured on 1000 ml ice-cold diethylether. The precipitated solid was collected by filtration and dried.

Yield: 24.9 g (98%) beige solid;

IR(KBr) 1782, 1680 cm$^{-1}$; MS(ISP) 466.4 (M+NH$_4$)$^+$.

According to the procedure set forth in the preceding example, the following additional compounds were prepared:

7.2. (E)-(6R,7R)-3-[(S)-1'-Allyloxycarbonyl-2-oxo-[1,3'] bipyrrolidinyl-3-ylidenemethy]-7-amino-8-oxo-5-thia-1-aza-bicyclo[4.2.0]oct-2-ene-2-carboxylic acid trifluoroacetate IR(KBr) 1782, 1679 cm$^{-1}$; MS(ISP) 466.3 (M+NH$_4$)$^+$.

7.3. Mixture of (E)-(6R,7R)-3-[(R)- and -[(S)-1'-allyloxycarbonyl-2-oxo-[1,3']bipyrrolidinyl-3-ylidenemethyl)-7-amino-8-oxo-5-thia-1-aza-bicyclo[4.2.0] oct-2-ene-2-carboxylic acid trifluoroacetate IR(KBr) 1783, 1678 cm$^{-1}$; MS(ISP) 449.5 (M+H)$^+$.

7.4. (E)-(6R,7R)-3-[1-(1-Allyloxycarbonyl-azetidin-3-yl)-2-oxo-pyrrolidin-3-ylidenemethyl]-7-amino-8-oxo-5-thia-1-aza-bicyclo[4.2.0]oct-2-ene-2-carboxylic acid trifluoroacetate IR(KBr) 1783, 1681 cm$^{-1}$; MS(ISP) 435.5 (M+H)$^+$.

7.5. (E)-(6R,7R)-3-[1-(1-Allyloxycarbonyl-piperidin-4-ylmethyl)-2-oxo-pyrrolidin-3-ylidenemethyl]-7-amino-8-oxo-5-thia-1-aza-bicyclo[4.2.0]oct-2-ene-2-carboxylic acid trifluoroacetate IR(KBr) 1784, 1681 cm$^{-1}$; MS(ISN) 492.3 (M-H+NH$_3$)$^-$.

7.6. (E)-(6R,7R)-7-Amino-3-[1-(1,2-bis-allyoxycarbonyl-pyrazolidin-4-yl)-2-oxo-pyrrolidin-3-ylidenemethyl]-8-oxo-5-thia-1-aza-bicyclo[4.2.0]oct-2-ene-2-carboxylic acid
m.p. 148–149∞C.

7.7. (E)-(6R,7R)-3-[1-[(S)-1-Allyloxycarbonyl-pyrrolidin-2-ylmethyl]-2-oxo-pyrrolidin-3-ylidenemethyl]-7-amino-8-oxo-5-thia-1-aza-bicyclo[4.2.0]oct-2-ene-2-carboxylic acid trifluoroacetate (1:0.2)

IR(KBr) 1780, 1690 cm$^{-1}$; MS(ISP) 463.3 (M+H)$^+$.

7.8. (E)-(6R,7R)-3-[1-[(3S,4R)-1-Allyloxycarbonyl-4-trifluoromethylpyrrolidin-3-ylmethyl]-2-oxo-pyrrolidin-3-ylidenemethyl]-7-amino-8-oxo-5-thia-1-aza-bicyclo[4.2.0]oct-2-ene-2-carboxylic acid IR(KIBr) 1779, 1686 cm$^{-1}$; MS(ISP) 531.3 (M+H)$^+$.

7.9. (E)-(6R,7R)-3-[(3'S,5'S)-1'-Allyloxycarbonyl-5'-dimethylcarbamoyl-2-oxo-[1,3']bipyrrolidinyl-3-ylidenemethyl)-7-amino-8-oxo-5-thia-1-aza-bicyclo[4.2.0]oct-2-ene-2-carboxylic acid trifluoroacetate (1:0.4)

IR(KBr) 1779, 1681 cm$^{-1}$; MS(ISP) 520.2 (M+H)$^+$.

7.10. (E)-(6R,7R)-3-[(3'S,5'R)-1'-Allyloxycarbonyl-5'-dimethylcarbamoyl-2-oxo-[1,3']bipyrrolidinyl-3-ylidenemethyl]-7-amino-8-oxo-5-thia-1-aza-bicyclo[4.2.0]oct-2-ene-2-carboxylic acid trifluoroacetate (1:0.5)

IR(KBr) 1779, 1681 cm$^{-1}$; MS(ISP) 520.3 (M+H)$^+$.

Example 8

8.1. (6R,7R)-3-[(E)-(R)-1'-Allyloxycarbonyl-2-oxo-[1,3']bipyrrolidinyl-3-ylidenemethyl]-7-[(Z)-2-(5-amino-[1,2,4]thiadiazol-3-yl)-2-trityloxyiminoacetylamino]-8-oxo-5-thia-1-aza-bicyclo[4.2.0]oct-2-ene-2-carboxylic acid was extracted with 150 ml ethyl acetate. The combined organic phases were concentrated upon which the product separated. It was collected by filtration, washed with ethyl acetate and dried.

Yield: 4.42 g (68%) beige crystals;

IR(KBr) 1785, 1681 cm$^{-1}$; MS(ISP) 878.6 (M+NH$_4$)$^+$.

According to the procedure set forth in the preceding example, the following additional compounds were prepared:

8.2. (6R,7R)-3-[(E)-(S)-1'-Allyloxycarbonyl-2-oxo-[1,3']bipyrrolidinyl-3-ylidenemethyl]-7-[(Z)-2-(5-amino-[1,2,4]thiadiazol-3-yl)-2-trityloxyiminoacetylamino]-8-oxo-5-thia-1-aza-bicyclo[4.2.0]oct-2-ene-2-carboxylic acid IR(KBr) 1784, 1680 cm$^{-1}$; MS(ISP) 878.6 (M+NH$_4$)$^+$.

8.3. Mixture of (6R,7R)-3-[(E)-(R)- and -(S)-1'-allyloxycarbonyl-2-oxo-[1,3']bipyrrolidinyl-3-ylidenemethyl]-7-[(Z)-2-(5-amino-[1,2,4]thiadiazol-3-yl)-2-trityloxyimino-acetylamino]-8-oxo-5-thia-1-aza-bicyclo[4.2.0]oct-2-ene-2-carboxylic acid IR(KBr) 1783, 1681 cm$^{-1}$; MS(ISP) 861.5 (M+H)$^+$.

8.4. (6R,7R)-3-[(E-1-(1-Allyloxycarbonyl-azetidin-3-yl)-2-oxo-pyrrolidin-3-ylidenemethyl]-7-[(Z)-2-(5-amino-[1,2,4]thiadiazol-3-yl)-2-trityloxyiminoacetylamino]-8-oxo-5-thia-1-aza-bicyclo[4.2.0]oct-2-ene-2-carboxylic acid IR(KBr) 1784, 1683 cm$^{-1}$; MS(ISP) 864.3 (M+NH$_4$)$^+$.

8.5. (6R,7R)-7-[(Z)-2-(5-Amino-[1,2,4]thiadiazol-3-yl)-2-trityloxyiraino-acetylamino]-3-[(E)-1-(1,2-bis-allyloxycarbonyl-pyrazolidin-4-yl)-3-oxo-pyrrolidin-3-ylidenemethyl]-8-oxo-5-thia-1-aza-bicyclo[4.2.0]oct-2-ene-2-carboxylic acid m.p. 184–185∞C.; MS(ISP) 946.1 (M+H)$^+$.

8.6. (6R,7R)-3-[(E)-1-[(S)-1-Allyloxycarbonyl-pyrrolidin-2-ylmethyl]-2-oxo-pyrrolidin-3-ylidenemethyl]-7-[(Z)-2-(5-amino-[1,2,4]thiadiazol-3-yl)-2-trityloxyimino-acetylamino]-8-oxo-5-thia-1-aza-bicyclo[4.2.0]oct-2-ene-2-carboxylic acid IR(KBr) 1790, 1681 cm$^{-1}$; MS(ISP) 875.4 (M+H)$^+$.

8.7. (6R,7R)-3-[(E)-1-[(3S,4R)-1-Allyloxycarbonyl-4-trifluoromethyl-pyrrolidin-3-ylmethyl]-2-oxo-pyrrolidin-3-ylidenemethyl]-7-[(Z)-2-(5amino-[1,2,4]thiadiazol-3-yl)-2-trityloxyimino-acetylamino]-8-oxo-5-thia-1-aza-bicyclo[4.2.0]oct-2-ene- 2-carboxylic acid

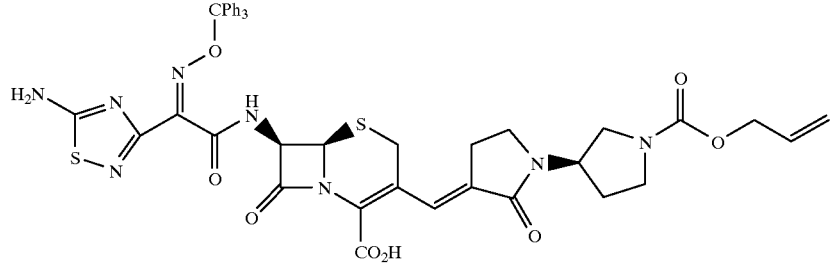

A solution of (E)-(6R,7R)-3-[(R)-1'-allyloxycarbonyl-2-oxo-[1,3']bipyrrolidinyl-3-ylidenemethy)-7-amino-8-oxo-5-thia-1-aza-bicyclo[4.2.0]oct-2-ene-2-carboxylic acid trifluoroacetate (3.90 g, 7.06 mmol)) in 75 ml DMF was treated with (Z)-(5-amino-[1,2,4]thiadiazol-3-yl)-trityloxyimino-thioacetic acid S-benzothiazol-2-yl ester (4.5 g, 7.76 mmol) for 48 h at room temperature. The reaction mixture was concentrated in vacuo and the residue distributed between 550 ml ethyl acetate and 375 ml water. The solid was discarded, the phases were separated and the aqueous phase IR(KBr) 1790, 1687 cm$^{-1}$; MS(ISP) 943.7 (M+H)$^+$.

Example 9

9.1. Mixture of (6R,7R)-3-[(E)-(R)- and -(S)-1'-allyloxycarbonyl-2-oxo-[1,3']bipyrrolidinyl-3-ylidenemethyl]-7-[(Z)-2-(2-amino-thiazol-4-yl)-2-trityloxyimino-acetylamino]-8-oxo-5-thia-1-aza-bicyclo[4.2.0]oct-2-ene-2-carboxylic acid

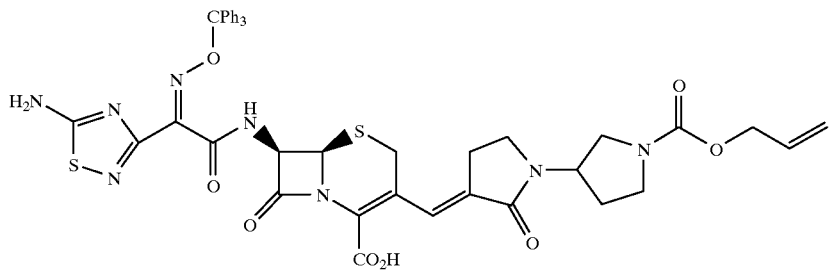

A solution of (E)-(6R,7R)-3-[(R)- and [(S)-1'-allyloxycarbonyl-2-oxo-[1,3']bipyrrolidinyl-3-ylidenemethyl]-7-amino-8-oxo-5-thia-1-aza-bicyclo[4.2.0]oct-2-ene-2-carboxylic acid trifluoroacetate (721 mg, 1.3 mmol) in 25 ml DMF was treated with (Z)-(2-aminothiazol-4-yl)-trityloxyimino-acetic acid 1-benzotriazolyl ester (782 mg, 1.43 mmol) at room temperature for 36 h. The reaction mixture was concentrated in vacuo and the residue distributed between 100 ml ethyl acetate and 50 ml water. The insoluble material was removed by filtration, the phases were separated and the organic phase was concentrated upon which the product precipitated. The solid was collected by filtration, washed with ethyl acetate and dried.

Yield: 725 mg (60%);

IR(IKBr) 1783, 1681 cm$^{-1}$; MS(ISP) 860.6 (M+H)$^+$.

According to the procedure set forth in the preceding example, the following additional compounds were prepared:

9.2. (6R,7R)-3-[(E)-(R)-1'-Allyloxycarbonyl-2-oxo-[1,3']bipyrrolidinyl-3-ylidenemethyl]-7-[(Z)-2-(2-amino-thiazol-4-yl)-2-trityloxyimino-acetylamino]-8-oxo-5-thia-1-aza-bicyclo[4.2.0]oct-2-ene-2-carboxylic acid IR(KBr) 1783, 1679 cm$^{-1}$; MS(ISP) 860.5 (M+H)$^+$.

9.3. (6R,7R)-3-[(E)-1-(1-Allyloxycarbonyl-azetidin-3-yl)-2-oxo-pyrrolidin-3-ylidenemethyl]-7-[(Z)-2-(2-amino-thiazol-4-yl)-2-trityloxyimino-acetylaminol-8-oxo-5-thia-1-aza-bicyclo[4.2.0]oct-2-ene-2-carboxylic acid IR(KBr) 1785, 1680 cm$^{-1}$; MS(ISP) 846.6 (M+H)$^+$.

9.4. (6R,7R)-3-[(E)-1-(Allyloxycarbonyl-piperidin-4-ylmethyl)-2-oxo-pyrrolidin-3-ylidenemethyl]-7-[(Z)-2-(2-amino-thiazol-4-yl)-2-trityloxyimino-acetylamino]-8-oxo-5-thia-1-aza-bicyclo[4.2.0]oct-2-ene-2-carboxylic acid IR(KBr) 1782, 1673 cm$^{-1}$; MS(ISP) 888.5 (M)$^+$.

9.5. (6R,7R)-3-[(E)-1-(1,2-bis-allyoxycarbonyl-pyrazolidin-4-yl)-2-oxo-pyrrolidin-3-ylidenemethyl]-7-[(Z)-2-(2-amino-thiazol-4-yl)-2-trityloxyimino-acetylamino]-8-oxo-5-thia-1-aza-bicyclo[4.2.0]oct-2-ene-2-carboxylic acid IR(KBr) 1756 cm$^{-1}$; MS(ISP) 536.3 (M+H)$^+$.

9.6. (6R,7R)-3-[(E)-1-[(3S,4R)-1-Allyloxycarbonyl-4-trifluoromethylpyrrolidin-3-ylmethyl]-2-oxo-pyrrolidin-3-ylidenemethyl]-7-[(Z)-2-(2-amino-thiazol-4-yl)-2-trityloxyimino-acetylamino]-8-oxo-5-thia-1-aza-bicyclo[4.2.0]oct-2-ene-2-carboxylic acid IR(KBr) 1790, 1686 cm$^{-1}$; MS(ISP) 942.4 (M+H)$^+$.

9.7. (6R,7R)-3-[(E)-1-[(S)-1-Allyloxycarbonyl-pyrrolidin-2-ylmethyl]-2-oxo-pyrrolidin-3-ylidenemethyl]-7-[(Z)-2-(2-amino-thiazol-4-yl)-2-trityloxyimino-acetylamino]-8-oxo-5-thia-1-aza-bicyclo[4.2.0]oct-2-ene-2-carboxylic acid IR(KBr) 1783, 1685 cm$^{-1}$; MS(ISP) 874.5 (M+H)$^+$.

Example 10

10.1. (6R,7R)-7-[(Z)-2-(5-Amino-[1,2,4]thiadiazol-3-yl)-2-trityloxyimino-acetyl-amino]-8-oxo-3-[(E)-(R)-2-oxo-[1,3'] bipyrrolidinyl-3-ylidenemethyl]-5-thia 1-aza-bicyclo[4.2.0] oct-2-ene-2-carboxylic acid dihydrochloride

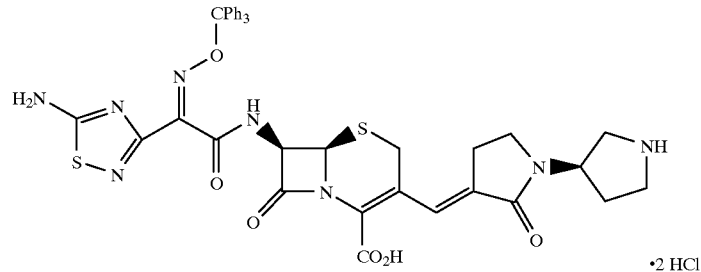

To a suspension of (6R,7R)-3-[(E)-(R)-1'-allyloxycarbonyl-2-oxo-[1,3']bi-pyrrolidinyl-3-ylidenemethyl]-7-[(Z)-2-(5-amino-[1,2,4]thiadiazol-3-yl)-2-trityloxyimino-acetylamino]-8-oxo-5-thia-1-aza-bicyclo[4.2.0]oct-2-ene-2-carboxylic acid (4.12 g, 4.79 mmol) in 280 ml dichloromethane was added 1.87 ml (7.66 mmol) N,O-bis(trimethylsilyl)acetamide whereby an orange solution formed which was subsequently treated with 84 mg (0.12 mmol) bis-(triphenylphosphine)-palladium(II)-dichloride, 5.48 ml (95.8 mmol) acetic acid and 11.7 ml (44.1 mmol) tributyltin hydride and stirred at room temperature for 40 min. After addition of a few drops of water, the suspension was poured on 1500 ml diethylether containing 12 ml of a solution of 6 M hydrogen chloride in diethylether. The suspension was stirred for 2 h and the product was collected by filtration.

Yield: 4.04 g (99%) beige solid;

IR(KBr) 1781, 1659 cm$^{-1}$; MS(ISP) 777.4 (M+H)$^+$.

According to the procedure set forth in the preceding example, the following additional compounds were prepared:

10.2. (6R,7R)-7-[(Z)-2-(5-Amino-[1,2,4]thiadiazol-3-yl)-2-trityloxyimino-acetyl-amino]-8-oxo-3-[(E)-(S)-2-oxo-[1,3']bipyrrolidinyl-3-ylidenemethyl]-5-thia-1-aza-bicyclo[4.2.0]oct-2-ene-2-carboxylic acid dihydro chloride IR(MIR) 1779, 1660 cm$^{-1}$; MS(ISP) 777.4 (M+H)$^+$.

10.3. Mixture of (6R,7R)-7-[(Z)-2-(5-amino-[1,2,4]thiadiazol-3-yl)-2-trityloxyimino-acetylamino]-8-oxo-3-[(E)-(R)- and -(S)-2-oxo-[1,3']bipyrrolidinyl-3-ylidenemethyl]-5-thia-1-aza-bicyclo[4.2.0]oct-2-ene-2-carboxylic acid dihydrochloride IR(KBr) 1780, 1660 cm$^{-1}$; MS(ISP) 777.3 (M+H)$^+$.

10.4. (6R,7R)-7-[(Z)-2-(5-Amino-[1,2,4]thiadiazol-3-yl)-2-trityloxyimino-acetyl-amino]-3-[(E)-1-azetidin-3-yl-2-oxo-pyrrolidin-3-ylidenemethyl]-8-oxo-5-thia-1-aza-bicyclo[4.2.0]oct-2-ene-2-carboxylic acid dihydrochloride IR(KBr) 1780, 1667 cm$^1$; MS(ISP) 763.3 (M+H)$^+$.

10.5. Mixture of (6R,7R)-7-[(Z)-2-(2-amino-thiazol-4-yl)-2-trityloxyimino-acetylamino]-8-oxo-3-[(E)-(R)- and -(S)-2-oxo-[1,3']bipyrrolidinyl-3-ylidenemethyl]-5-thia-1-aza-bicyclo[4.2.0]oct-2-ene-2-carboxylic acid dihydrochloride IR(KBr) 1780, 1659 cm$^{-1}$; MS(ISP) 776.4 (M+H)$^+$.

10.6. (6R,7R)-7-[(Z)-2-(2-Amino-thiazol-4-yl)-2-trityloxyimino-acetylamino]-3-[(E)-1-azetidin-3-yl-2-oxo-pyrrolidin-3-ylidenemethyl]-8-oxo-5-thia-1-aza-bicyclo[4.2.0]oct-2-ene-2-carboxylic acid dihydrochloride IR(KBr) 1780, 1661 cm$^{-1}$; MS(ISP) 762.5 (M+H)$^+$.

10.7. (6R,7R)-7-[(Z)-2-(2-Amino-thiazol-4-yl)-2-trityloxyimino-acetylamino]-8-oxo-3-[(E)-2-oxo-1-piperidin-4-ylmethyl-pyrrolidin-3-ylidenemethyl]-5-thia-1-aza-bicyclo[4.2.0]oct-2-ene-2-carboxylic acid dihydrochloride IR(KBr) 1778, 1661, 1631 cm$^{-1}$; MS(ISP) 804.7 (M+H)$^+$.

10.8. (6R,7R)-7-[(Z)-2-(5-Amino-[1,2,4]thiadiazol-3-yl)-2-trityloxyimino-acetylamino]-8-oxo-3-[(E)-2-oxo-1-pyrazolidin-4-yl-pyrrolidin-3-ylidenemethyl]-5-thia-1-aza-bicyclo[4.2.0]oct-2-ene-2-carboxylic acid hydrochloride (1:1)

m.p. 163–164° C.; IR(KBr) 1785 cm$^{-1}$; MS(ISP) 778.4 (M+H)$^+$.

10.9. (6R,7R)-7-[(Z)-2-(5-Amino-[1,2,4]thiadiazol-3-yl)-2-trityloxyimino-acetylamino]-8-oxo-3-[(E)-1-oxo-2-[(3R,4R)-4-trifluoromethyl-pyrrolidin-3-ylmethyl]-pyrrolidin-3-ylidenemethyl]-5-thia-1-aza-bicyclo[4.2.0]oct-2-ene-2-carboxylic acid hydrochloride (1:2)

IR(KBr) 1790, 1633 cm$^{-1}$; MS(ISP) 859.4 (M+H)$^+$.

Example 11

11.1. (6R,7R)-7-[(Z)-2-(5-Amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-10 aza-bicyclo[4.2.0]oct-2-ene-2-carboxylic acid To a solution of (6R,7R)-7-[(Z)-2-(5-amino-[1,2,4]thiadiazol-3-yl)-2-trityloxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid dihydrochloride (4.04 g, 4.76 mmol) in 26 ml trifluoroacetic acid was added at 0–5° C. 1.69 ml triethylsilane and the mixture was stirred for 30 min. The reaction mixture was poured with stirring on 780 ml ice-cold diethylether upon which the product separated as a beige solid. After stirring for 1 h, the solid was collected by filtration and dried. The product was purified by gel chromatography (MCI Gel 75–150µ, using a gradient of water with increasing concentrations of acetonitrile).

Yield: 1.24 g (49%).

IR(MIR) 1764, 1658 cm$^{-1}$; MS(ISP) 535.1 (M+H)$^+$.

1H-NMR(DMSO, 250 MHz): inter alia δ 1.92–2.16 (m, 2H); 3.60 (d,J=17 Hz,1H); 3.79 (d,J=17 Hz, 1H); 4.66, (m, 1H); 5.07 (d,J=8 Hz, 1H); 5.75 (dd,J=5 Hz, J=8 Hz 1H); 7.30 (s, 1H); 8.05 (s, 2H); 9.46 (d,J=8 Hz, 1H); 10.3 (s br, 1H); 12.0 (s br, 1H) ppm.

According to the procedure set forth in the preceding example, the following additional compounds were prepared:

11.2. (6R,7R)-7-[(Z)-2-(5-Amino-[1,2,4]thiadiazol-3-yl)-2-hydroxyimino-acetylamino]-8-oxo-3-[(E)-(S)-2-oxo-[1,3']bipyrrolidinyl-3-ylidenemethyl]-5-thia-1-aza-bicyclo[4.2.0]oct-2-ene-2-carboxylic acid IR(KBr) 1766, 1687 cm$^{-1}$; MS(ISP) 535.2 (M+H)$^+$.

1H-NMR(DMSO, 250 MHz): inter alia δ 1.92–2.16 (m, 2H); 3.69 (s, 2H); 4.58 (m, 1H), 5.08 (d J=8 Hz, 1H); 5.75 (dd,J=5 Hz, J=8 Hz, 1H); 7.30 (s, 1H); 8.05 (s, 2H); 9.44 (d,J=8 Hz, 1H); 10 (s br, 1H) ppm.

11.3. Mixture of (6R,7R)-7-[(Z)-2-(5-amino-[1,2,4]thiadiazol-3-yl)-2-hydroxyimino-acetylamino]-8-oxo-3-[(E)-(R)- and -(S)-2-oxo-[1,3']bipyrrolidinyl-3-ylidenemethyl]-5-thia-1-aza-bicyclo[4.2.0]oct-2-ene-2-carboxylic acid IR(KBr) 1765, 1659 cm$^{-1}$; MS(ISP) 535.3 (M+H)$^+$.

11.4. (6R,7R)-7-[(Z)-2-(5-Amino-[1,2,4]thiadiazol-3-yl)-2-hydroxyimino-acetylamino]-3-[(E)-1-azetidin-3-yl-2-oxo-pyrrolidin-3-ylidenemethyl]-8-oxo-5-thia-1-aza-bicyclo[4.2.0]oct-2-ene-2-carboxylic acid IR(KBr) 1762, 1689, 1668 cm$^{-1}$; MS(ISP) 521.2 (M+H)$^+$.

11.5. (6R,7R)-7-[(Z)-2-(2-Amino-thiazol-4-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid IR(KBr) 1766, 1670 cm$^{-1}$; MS(ISP) 534.2 (M+H)$^+$.

11.6. Mixture of (6R,7R)-7-[(Z)-2-(2-amino-thiazol-4-yl)-2-hydroxyimino-acetylamino]-8-oxo-3-[(E)-(R)- and -(S)-2-oxo-[1,3']bipyrrolidinyl-3-ylidenemethyl]-5-thia-1-aza-bicyclo[4.2.0]oct-2-ene-2-carboxylic acid dihydrochloride IR(KBr) 1775, 1667 cm$^{-1}$; MS(ISP) 534.3 (M+H)$^+$.

11.7. (6R,7R)-7-[(Z)-2-(2-Amino-thiazol-4-yl)-2-hydroxyimino-acetylaminol-3-[(E)-1-azetidin-3-yl-2-oxo-pyrrolidin-3-ylidenemethyl]-8-oxo-5-thia-1-aza-bicyclo[4.2.0]oct-2-ene-2-carboxylic acid dihydrochloride IR(KBr) 1776, 1669 cm$^{-1}$; MS(ISP) 520.2 (M+H)$^+$.

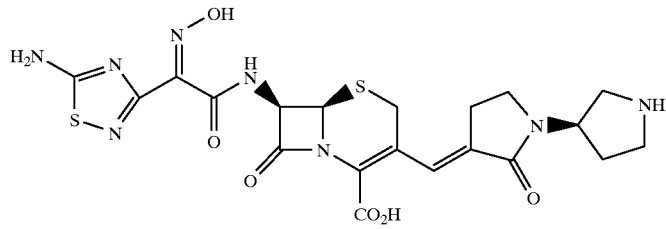

11.8. (6R,7R)-7-[(Z)-2(2-Amino-thiazol-4-yl)-2-hydroxyimino-acetylamino]-8-oxo-3-[(E)-2-oxo-1-piperidin-4-ylmethyl-pyrrolidin-3-ylidenemethyl-5-thia-1-aza-bicyclo[4.2.0]oct-2-ene-2-carboxylic acid trifluoroacetate IR(KBr) 1774, 1664 cm$^{-1}$; MS(ISP) 562.4 (M+H)$^+$.

11.9. 7-[(Z)-2-(5-Amino-[1,2,4]thiadiazol-3-yl)-2-hydroxyimino-acetylamino]-8-oxo-3-[(E)-2-oxo-1-pyrazolidin-4-yl-pyrrolidin-3-ylidenemethyl]-5-thia-1-aza-bicyclo[4.2.0]oct-2-ene-2-carboxylic acid IR(KBr) 1756 cm$^{-1}$; MS(ISP) 536.3 (M+H)$^+$.

11.10. (6R,7R)-7-[(Z)-2-(2-amino-thiazol-4-yl)-2-hydroxyimino-acetylamino]-8-oxo-3-[(E)-2-oxo-1-pyrazolidin-4-yl-pyrrolidin-3-ylidenemethyl]-5-thia-1-aza-bicyclo[4.2.0]oct-2-ene-2-carboxylic acid m.p. 239–240° C.;

IR(KBr) 1764 cm$^{-1}$; MS(ISP) 535.3 (M+H)$^+$.

11.11. (6R,7R)-7-[(Z)-2-(5-Amino-[1,2,4]thiadiazol-3-yl)-2-hydroxyimino-acetylamino]-8-oxo-3-[(E)-(S)-(2-oxo-1-pyrrolidin-2-ylmethyl-pyrrolidin-3-ylidenemethyl)]-5-thia-1-aza-bicyclo[4.2.0]oct-2-ene-carboxylic acid IR(KBr) 1785, 1624 cm$^{-1}$; MS(ISP) 549.1 (M+H)$^+$.

11.12. (6R,7R)-7-[(Z)-2-(2-Amino-thiazol-4-yl)-2-hydroxyimino-acetylamino]-8-oxo-3-[(E)-(S)-(2-oxo-1-pyrrolidin-2-ylmethyl-pyrrolidin-3-ylidenemethyl)]-5-thia-1-aza-bicyclo[4.2.0]oct-2-ene-carboxylic acid IR(KBr) 1767 cm$^{-1}$; MS(ISP) 548.2 (M+H)$^+$.

11.13. (6R,7R)-7-[(Z)-2-(2-Amino-thiazol-4-yl)-2-hydroxyimino-acetylaminol-8-oxo-3-[(E)-2-oxo-1-[(3R,4R)-4-trifluoromethyl-pyrrolidin-3-ylmethyl]-pyrrolidin-3-ylidenemethyl]-5-thia-1-aza-bicyclo[4.2.0]oct-2-ene-2-carboxylic acid IR(KBr) 1770, 1665 cm$^{-1}$; MS(ISP) 616.3 (M+H)$^+$.

11.14. (6R,7R)-7-[(Z)-2-(5-Amino-[1,2,4]thiadiazol-3-yl)-2-hydroxyimino-acetylamino]-8-oxo-3-[(E)-2-oxo-1-[(3R,4R)-4-trifluoromethyl-pyrrolidin-3-ylmethyl]-pyrrolidin-3-ylidenemethyl]-5-thia-1-aza-bicyclo[4.2.0]oct-2-ene-2-carboxylic acid IR(KBr) 1768, 1625 cm$^{-1}$;

11.15. (6R,7R)-7-[(Z)-2-(5-Amino-[1,2,4]thiadiazol-3-yl)-2-hydroxyimino-acetylaminol-3-[(E)-(3'S,5'R)-5'-dimethylcarbamoyl-2-oxo-([1,3']bipyrrolidinyl-3-ylidenemethyl]-8-oxo-5-thia-1-aza-bicyclo[4.2.0]oct-2-ene-2-carboxylic acid IR(KBr) 1768, 1656 cm$^{-1}$; MS(ISP) 606.1 (M+H)$^+$.

11.16. (6R,7R)-7-[(Z)-2-(5-Amino-[1,2,4]thiadiazol-3-yl)-2-hydroxyimino-acetylamino]-3-[(E)-(3'S,5'S)-5'dimethylcarbamoyl-2-oxo-[1,3']bipyrrolidinyl-3-ylidenemethyl]-8-oxo-5-thia-1-aza-bicyclo[4.2.0]oct-2-ene-2-carboxylic acid formate (1:1)

IR(KBr) 1768 cm$^{-1}$; MS(ISP) 606.1 (M+H)$^+$.

11.17. (6R,7R)-7-[(Z)-2-(2-Amino-thiazol-4-yl)-2-hydroxyimino-acetylamino]-3-[(E)-(3'S,5'R)-5'-dimethylcarbamoyl-2-oxo-[1,3']bipyrrolidinyl-3-ylidenemethyl]-8-oxo-5-thia-1-aza-bicyclo[4.2.0]oct-2-ene-2-carboxylic acid IR(KBr) 1766, 1656 cm$^{-1}$; MS(ISP) 605.3 (M+H)$^+$.

11.18. (6R,7R)-7-[(Z)-2-(2-Amino-thiazol-4-yl)-2-hydroxyimino-acetylamino]-3-[(E)-(3'S,5'S)-5'-dimethylcarbamoyl-2-oxo-[1,3']bipyrrolidinyl-3-ylidenemethyl]-8-oxo-5-thia-1-aza-bicyclo[4.2.0]oct-2-ene-2-carboxylic acid IR(KBr) 1767, 1657 cm$^{-1}$; MS(ISP) 605.1 (M+H)$^+$.

Example 12

12.1. Mixture of (6R,7R)-7-[(Z)-2-(5-amino-[1,2,4]thiadiazol-3-yl)-2-cyclopentyloxyimino-acetylamino]-8-oxo-3-[(E)-(R)- and -(S)-2-oxo-[1,3']bipyrrolidinyl-3-ylidenemethyl]-5-thia-1-aza-bicyclo[4.2.0]oct-2-ene-2-carboxylic acid

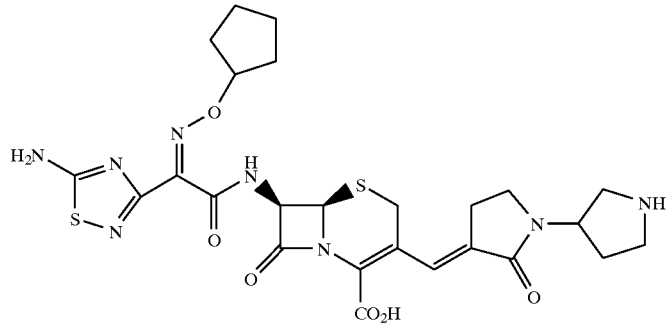

To a suspension of 454 mg (1.19 mmol) (Z)-(5-amino-[1,2,4]thiadiazol-3-yl)-cyclopentyloxyimino-acetate 1-allyl-1-methyl-pyrrolidinium salt in 9.5 ml dimethylformamide was added 451 mg (1.19 mnol) O-benzotriazol-1-yl-N,N,N',N'-tetramethyluronium-hexafluorophosphate (HBTU) and the mixture was stirred for 1 h. To the resulting orange solution was added a mixture of (E)-(6R,7R)-3-[(R)- and -[(S)-1'-allyloxycarbonyl-2-oxo-[1,3']bi-pyrrolidinyl-3-ylidenemethy)-7-amino-8-oxo-5-thia-1-aza-bicyclo[4.2.0] oct-2-ene-2-carboxylic acid trifluoroacetate (600 mg, 1.08 mmol) and the mixture was stirred for 40 h at room temperature. The reaction mixture was concentrated in vacuo and the residue distributed between 100 ml ethyl acetate and 70 ml water. The phases were separated and the organic phase was concentrated upon which the product precipitated. The solid was collected by filtration, washed with ethyl acetate and dried, yielding 291 mg (39%) of a beige amorphous powder. Removal of the allyloxycarbonyl protective group was accomplished according to example 9. The product was purified by gel chromatography (MCI Gel 75–150μ, using a gradient of water with increasing concentrations of acetonitrile).

Yield: 40 mg (16%) beige solid;

IR(KBr) 1771, 1672 cm$^{-1}$; MS(ISP) 603.3 (M+H)$^+$.

12.2. (6R,7R)-7-[(Z)-2-(5-Amino-[1,2,4]thiadiazol-3-yl)-2-cyclopentyloxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid IR(KBr) 1777, 1670 cm$^{-1}$; MS(ISP) 603.2 (M+H)$^+$.

Example 13

13.1. Mixture of (6R,7R)-3-[(E)-(R)- and -(S)-1'-allyloxycarbonyl-2-oxo-[1,3']bi-pyrrolidinyl-3- ylidenemethyl]-7-[(Z)-2-(2-amino-thiazol-4 -yl)-2-cyclopentyloxyimino-acetylamino]-8-oxo-5-thia-1-aza-bicyclo[4.2.0]oct-2-ene-2-carboxylic acid -(S)-2-oxo-[1,3']bipyrrolidinyl-3-ylidenemethyl]-5-thia-1-aza-bicyclo[4.2.0]oct-2-ene-2-carboxylic acid

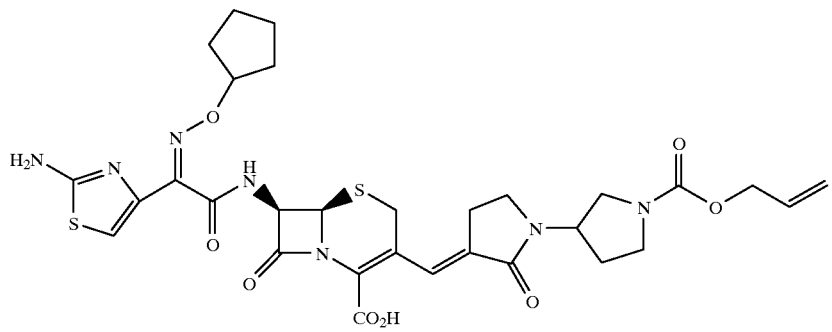

A suspension of (E)-(6R,7R)-3-[(R)- and [(S)-1'-allyloxycarbonyl-2-oxo-[1,3']bi-pyrrolidinyl-3-

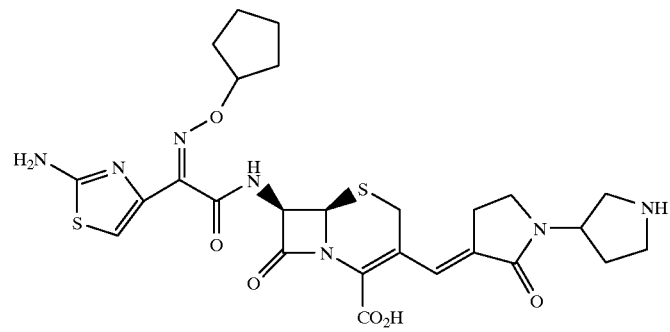

ylidenemethyl]-7-amino-8-oxo-5-thia-1-aza-bicyclo[4.2.0]oct-2-ene-2-carboxylic acid trifluoroacetate (555 mg, 1.0 mmol) in 20 ml DMF was treated for 12 h at room temperature with (Z)-(2-aminothiazol-4-yl)-cyclopentyloxyimino-thioacetic acid S-benzothiazol-2-yl ester (445 mg, 1.1 mmol). The reaction mixture was concentrated in vacuo and the residue triturated in a mixture of 70 ml ethyl acetate and 50 ml water. The solid was collected by filtration, washed with water, ethyl acetate and dried.

Yield: 484 mg (71%).
IR(KBr) 1778, 1677, 1629 cm$^{-1}$; MS(ISP) 686.4 (M+H)$^+$.

According to the procedure set forth in the preceding example, the following additional compounds were prepared:

13.2 (6R,7R)-3-[(E)-1-(1-Allyloxycarbonyl-azetidin-3-yl)-2-oxo-pyrrolidin-3-ylidenemethyl]-7-[(Z)-2-(2-amino-thiazol-4-yl)-2-cyclopentyloxyimino-acetylamino]-8-oxo-5-thia-1-aza-bicyclo[4.2.0]oct-2-ene-2-carboxylic acid
IR(KBr) 1774, 1673 cm$^{-1}$; MS(ISP) 672.4 (M+H)$^+$.

13.3. (6R,7R)-3-[(E)-1-(Allyloxycarbonyl-piperidin-4-ylmethyl)-2-oxo-pyrrolidin-3-ylidenemethyl]-7-[(Z)-2-(2-amino-thiazol-4-yl)-2-cyclopentyloxyimino-acetylamino]-8-oxo-5-thia-1-aza-bicyclo[4.2.0]oct-2-ene-2-carboxylic acid
IR(KBr) 1779, 1676, 1630 cm$^{-1}$; MS(ISP) 714.5 (M+H)$^+$.

Example 14
14.1. Mixture of (6R,7R)-7-[(Z)-2-(2-amino-thiazol-4-yl)-2-cyclopentyloxyimino-acetylamino]-8-oxo-3-[(E)-(R)- and Removal of the allyloxycarbonyl-protective group in the mixture of (6R,7R)-3-[(E)-(R)- and -(S)-1'-allyloxycarbonyl-2-oxo-[1,3']bipyrrolidinyl-3-ylidene-methyl]-7-[(Z)-2-(2-amino-thiazol-4-yl)-2-cyclopentyloxyimino-acetylamino]-8-oxo-5-thia-1-aza-bicyclo[4.2.0]oct-2-ene-2-carboxylic acids was accomplished using the procedure described in example 9. The crude product (328 mg) was purified by gel chromatography (MCI Gel 75–150µ, using a gradient of water with increasing concentrations of acetonitrile). The pure product crystallized from the chromatographic fractions and was collected by filtration.

Yield: 102 mg (28%) yellow crystals;
IR(KBr) 1770, 1666, 1625 cm$^{-1}$; MS(ISP) 602.4 (M+H)$^+$.

According to the procedure set forth in the preceding example, the following additional compounds were prepared:

14.2. (6R,7R)-7-[(Z)-2-(2-Amino-thiazol-4-yl)-2-cyclopentyloxyimino-acetylamino]-3-(E)-1-azetidin-3-yl-2-oxo-pyrrolidin-3-ylidenemethyl]-8-oxo-5-thia-1-aza-bicyclo[4.2.0]oct-2-ene-2-carboxylic acid dihydrochloride
IR(KBr) 1780, 1661 cm$^{-1}$; MS(ISP) 588.3 (M+H)$^+$.

14.3. (6R,7R)-7-[(Z)-2-(2-Amino-thiazol-4-yl)-2-cyclopentyloxyimino-acetylamino]-8-oxo-3-[(E)-2-oxo-1-piperidin-4-ylmethyl-pyrrolidin-3-ylidenemethyl]-5-thia-1-aza-bicyclo[4.2.0]oct-2-ene-2-carboxylic acid hydrochloride
IR(KBr) 1771, 1665, 1627 cm$^{-1}$; MS(ISP) 630.6 (M+H)$^+$.

Example 15

(6R,7R)-7-[(Z)-2-(5-Amino-[1,2,4]thiadiazol-3-yl)-2-hydroxyimino-acetylamino]-3-[(E)-(R)-1'-iminomethyl-2-oxo-[1,3']bipyrrolidinyl-3-ylidenemethyl]-8-oxo-5-thia-1-aza-bicyclo[4.2.0]oct-2-ene-2-carboxylic acid

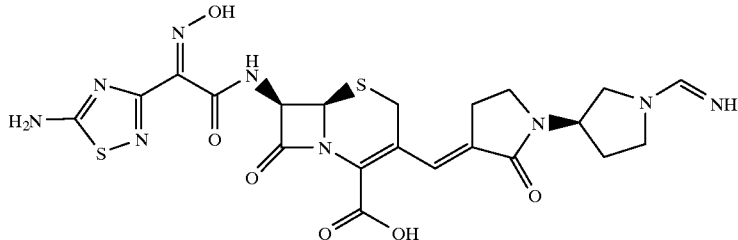

To a suspension of 66 mg sodium hydride (65% in mineral oil) in 2 ml DMSO was added 200 mg of ethylformimidate hydrochloride and 100 mg (0.2 mmol) (6R,7R)-7-[(Z)-2-(5-Amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid. The reaction mixture was stirred for 30 min. at room temperature before it was hydrolyzed with some drops of water. It was purified by reversed-phase chromatography on MCI gel by elution with water:acetonitrile=9:1.

Yield: 30 mg;
IR(KBr) 1767 cm$^{-1}$; MS(ISP) 562. 2 (M+H)$^+$.

Example 16

(6R,7R)-7-[(Z)-2-(5-Amino-[1,2,4]thiadiazol-3-yl)-2-hydroxyimino-acetylamino]-3-[(E)-((R)-1'-carbamimidoyl-2-oxo-[1,3']bipyrrolidinyl-3-ylidenemethyl)]-8-oxo-5-thia-1-aza-bicyclo[4.2.0]oct-2-ene-2-carboxylic acid

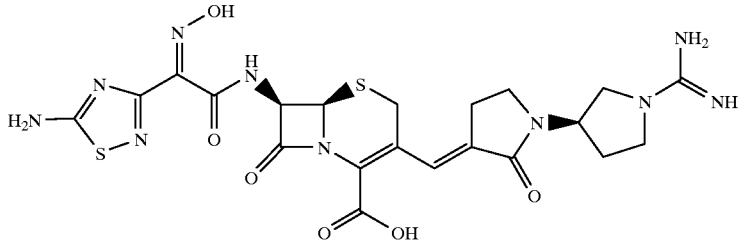

To a solution of 150 mg [1,2,4]triazole-1-carboxamidine hydrochloride in 1 ml DMSO were added 13 ml tetramethylguanidine and 53 mg (6R,7R)-7-[(Z)-2-(5-amino-(1,2,4] thiadiazol-3-yl)-2-hydroxyimino-acetylaminol-8-oxo-3-[(E)-(R)-2-oxo-[1,3']bipyrrolidinyl-3-ylidenemethyl)-5-thia-1-aza-bicyclo[4.2.0]oct-2-ene-2-carboxylic acid. After 1 h stirring at room temperature, the reaction mixture was purified by reversed-phase chromatography on MCI gel by elution with water:acetonitrile=9:1.

Yield: 30 mg;

IR(KBr) 1769 cm$^{-1}$; MS(ISP) 577.0 (M+H)$^+$.

Example 17

Following the procedures set forth in the above Examples the following compounds can be prepared:

17.1. (6R,7R)-7-[(Z)-2-(5-Amino-[1,2,4]thiadiazol-3-yl)-2-hydroxyimino-acetylamino]-3-[(E)-5'-hydroxymethyl-2-oxo-[1,3']bipyrrolidinyl-3-ylidenemethyl]-8-oxo-5-thia-1-aza-bicyclo[4.2.0]oct-2-ene-2-carboxylic acid

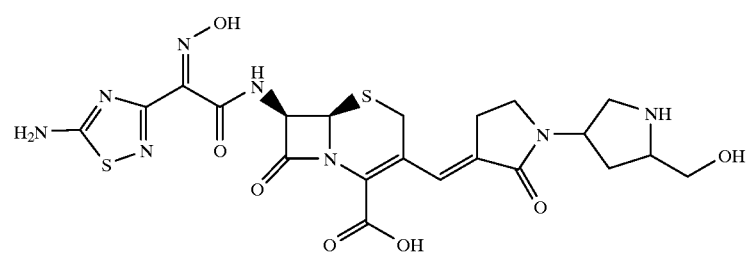

17.2. (6R, 7R)-3-[(E)-5'-Aminomethyl-2-oxo-[1,3']bipyrrolidinyl-3-ylidenemethyl]-7-[(Z)-2-(5-amino-[1,2,4]thiadiazol-3-yl)-2-hydroxyimino-acetylamino]-8-oxo-5-thia-1-aza-bicyclo[4.2.0]oct-2-ene-2-carboxylic acid

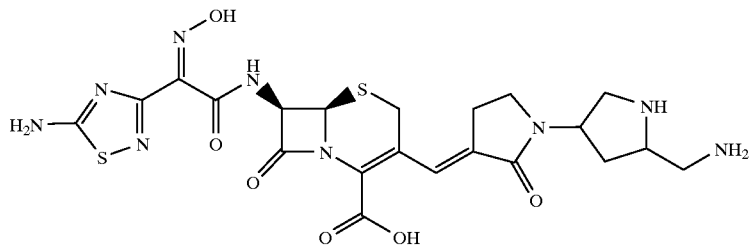

17.3. (6R,7R)-7-[(Z)-2-(5-Amino-[1,2,4]thiadiazol-3-yl)-2-hydroxyimnino-acetylaminol-8-oxo-3-[(E)-2-oxo-5'-pyridin-1-ium-1-ylmethyl-[1,3']bipyrrolidinyl-3-ylidenemethyl]-5-thia-1-aza-bicyclo[4.2.0]oct-2-ene-2-carboxylate

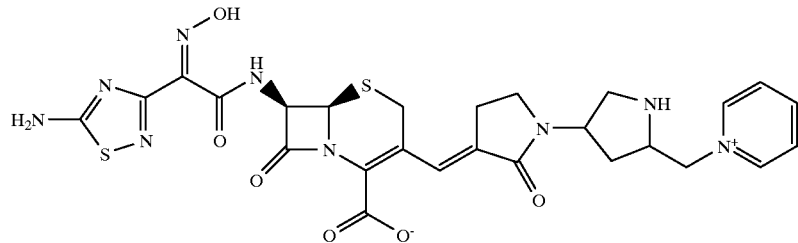

17.4. (6R,7R)-7-[(Z)-2-(5-Amino-[1,2,4]thiadiazol-3-yl)-2-hydroxyimino-acetylamino]-3-[(E)-5'-(1-hydroxy-3-methylamino-propyl)-2-oxo-[1,3]bipyrrolidinyl-3-ylidenemethyl]8-thia-1-aza-bicyclo[4.2.0]oct-2-ene-2-carboxylic acid

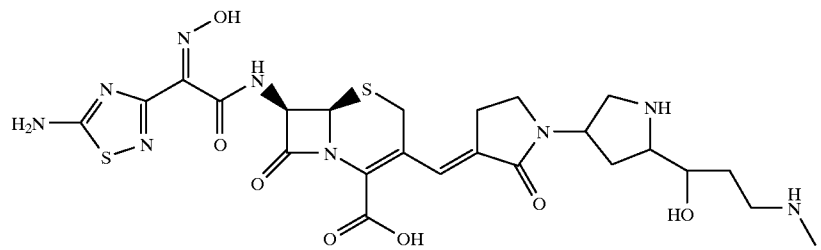

17.5. (6R,7R)-7-[(Z)-2-(5-Amino-[1,2,4]thiadiazol-3-yl)-2-hydroxyimino-acetylamino]-3-[(E)-4'-hydroxy-2-oxo-[1,3']bipyrrolidinyl-3-ylidenemethyl]-8-oxo-5-thia-1-aza-bicyclo[4.2.0]oct-2-ene-2-carboxylic acid

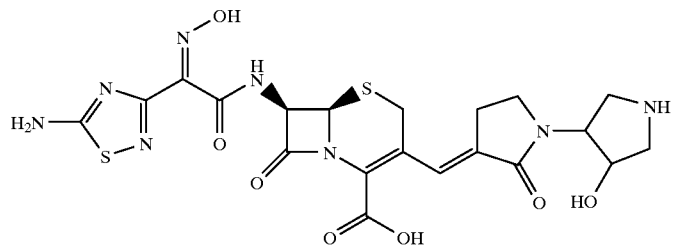

17.6. (6R,7R)-7-[(Z)-2-(5-Amino-[1,2,4]thiadiazol-3-yl)-2-hydroxyimino-acetylamino]-3-[(E)-5'-(hydroxy-pyrrolidin-2-yl-methyl)-2-oxo-[1,3']bipyrrolidinyl-3-ylidenemethyl]-8-oxo-5-thia-1-aza-bicyclo[4.2.0]oct-2-ene-2-carboxylic acid

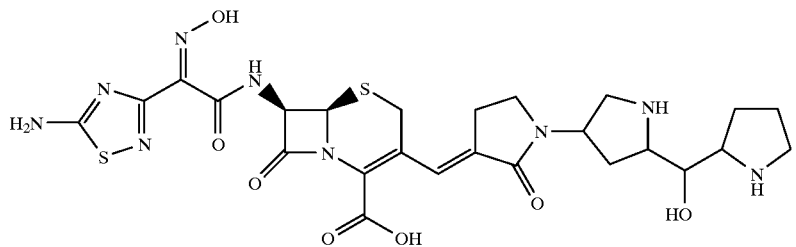

17.7. (6R,7R)-7-[(Z)-2-(5-Amino-[1,2,4]thiadiazol-3-yl)-2-hydroxyimino-acetylamino]-8-oxo-3-[(E)-2-oxo-1-pyrrolidin-3-ylmethyl-pyrrolidin-3-ylidenemethyl]-5-thia-1-aza-bicyclo[4.2.0]oct-2-ene-2-carboxylic acid

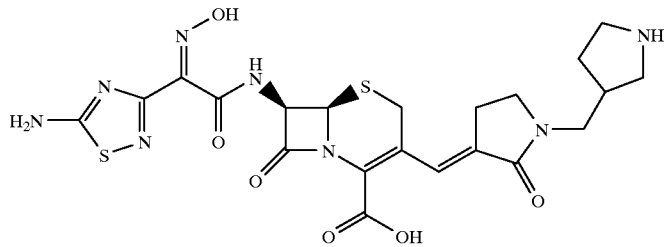

17.8. (6R,7R)-7-[(Z)-2-(5-Amino-[1,2,4]thiadiazol-3-yl)-2-hydroxyimino-acetylaminol-3-[(E)-1-azetidin-3-ylmethyl-2-oxo-pyrrolidin-3-ylidenemethyl]-8-oxo-5-thia-1-aza-bicyclo[4.2.0]oct-2-ene-2-carboxylic acid

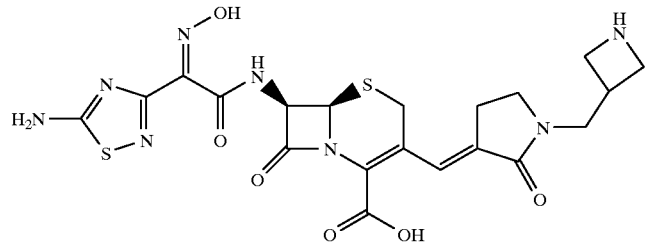

17.9. (6R,7R)-7-[(Z)-2-(5-Amino-[1,2,4]thiadiazol-3-yl)-2-hydroxyimino-acetylamino]-3-[(E)-1'-azetidin-3-ylmethyl-2-oxo-[1,3']bipyrrolidinyl-3-ylidenemethyl]-8-oxo-5-thia-1-aza-bicyclo[4.2.0]oct-2-ene-2-carboxylic acid

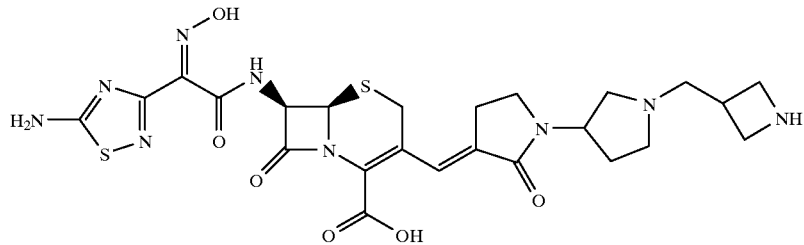

17.10. (6R,7R)-7-[(Z)-2-(5-Amino-[1,2,4]thiadiazol-3-yl)-2-hydroxyimino-acetylamino]-8-oxo-3-[(E)-2-oxo-1'-pyrrolidin-2-ylmethyl-[1,3']bipyrrolidinyl-3-ylidenemethyl]-5-thia-1-aza-bicyclo[4.2.0]oct-2-ene-2-carboxylic acid

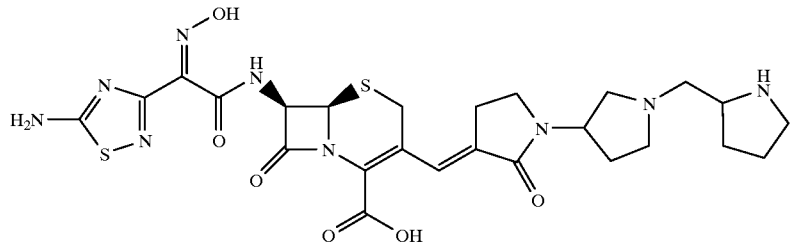

17.11. (6R,7R)-7-[(Z)-2-(5-Arnino-[1,2,4]thiadiazol-3-yl)-2-hydroxyimino-acetylamino]-3-[(E)-1-[2-(2-hydroxy-ethylamino)-ethyl]-2-oxo-pyrrolidin-3-ylidenemethyl]-8-oxo-5-thia-1-aza-bicyclo[4.2.0]oct-2-ene-2-carboxylic acid

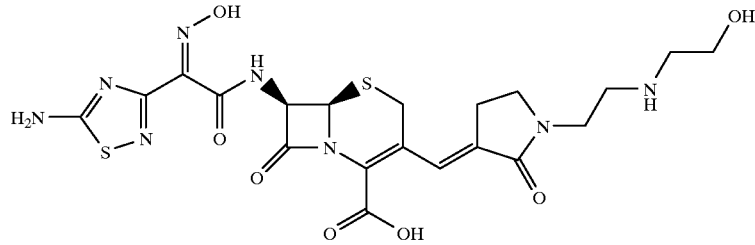

17.12. (6R,7R)-7-[(Z)-2-(5-Amino-[1,2,4]thiadiazol-3-yl)-2-hydroxyimino-acetylamino]-3-[(E)-1-(2-methylamino-ethyl)-2-oxo-pyrrolidin-3-ylidenemethyl]-8-oxo-5-thia-1-aza-bicyclo[4.2.0]oct-2-ene-2-carboxylic acid

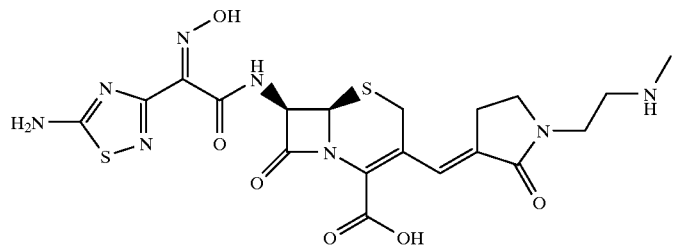

17.13. (6R,7R)-7-[(Z)-2-(5-Amino-[1,2,4]thiadiazol-3-yl)-2-hydroxyimino-acetylamino]-3-[(E)-1-(2-cyclopropylamino-ethyl)-2-oxo-pyrrolidin-3-ylidenemethyl]-8-oxo-5-thia-1-aza-bicyclo[4.2.0]oct-2-ene-2-carboxylic acid

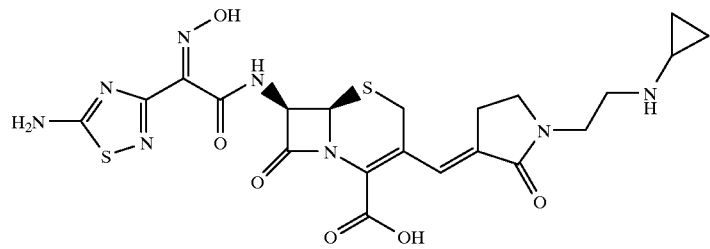

17.14. (6R, 7R)-7-[(Z)-2-(5-Amino-[1,2,4]thiadiazol-3-yl)-2-hydroxyimino-acetylamino]-3-[(E)-1-[2-(iminomethylamino)-ethyl]-2-oxo-pyrrolidin-3-ylidenemethyl]-8-oxo-5-thia-1-aza-bicyclo[4.2.0]oct-2-ene-2-carboxylic acid

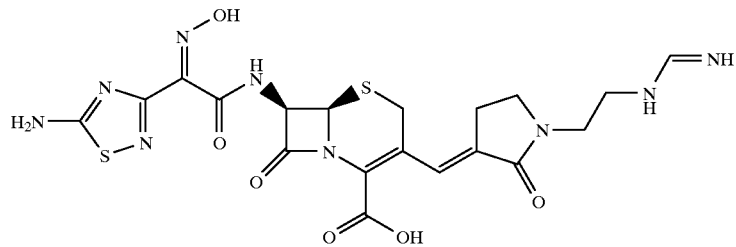

17.15. (6R,7R)-7-[(Z)-2-(5-Amino-[1,2,4]thiadiazol-3-yl)-2-hydroxyimino-acetylamino]-3-[(E)-1-(2-guanidino-ethyl)-2-oxo-pyrrolidin-3-ylidenemethyl]-8-oxo-5-thia-1-aza-bicyclo[4.2.0]oct-2-ene-2-carboxylic acid

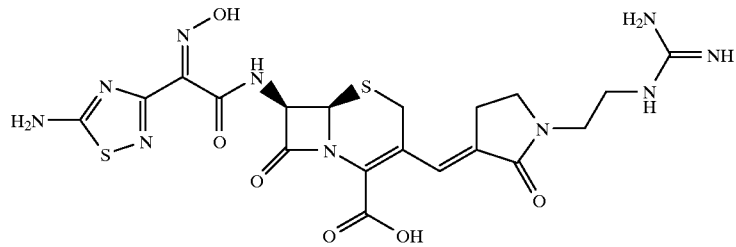

17.16. (6R,7R)-7-[(Z)-2-(5-Amino-[1,2,4]thiadiazol-3-yl)-2-hydroxyimino-acetylamino]-8-oxo-3-[(E)-2-oxo-1-(2-piperazin-1-yl-ethyl)-pyrrolidin-3-ylidenemethyl]-5-thia-1-aza-bicyclo[4.2.0]oct-2-ene-2-carboxylic acid

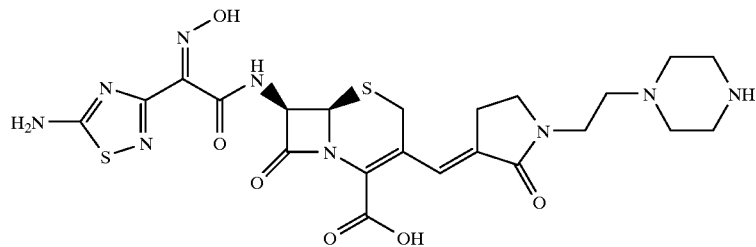

17.17. (6R,7R)-7-[(Z)-2-(5-Amino-[1,2,4]thiadiazol-3-yl)-2-hydroxyimino-acetylamino]-8-oxo-3-[(E)-2-oxo-1-[2-(pyrrolidin-3-ylamino)-ethyl]-pyrrolidin-3-ylidenemethyl]-5-thia-1-aza-bicyclo[4.2.0]oct-2-ene-2-carboxylic acid

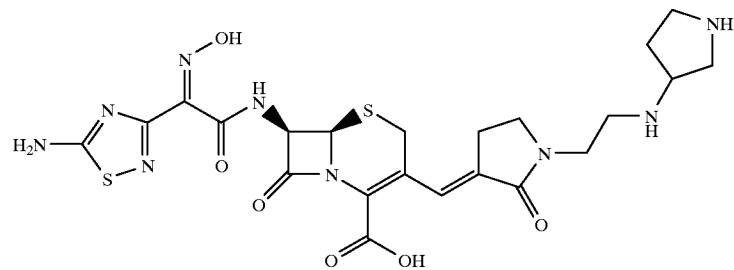

17.18. (6R,7R)-7-[(Z)-2-(5-Amino-[1,2,4]thiadiazol-3-yl)-2-hydroxyimino-acetylamino]-3-[(E)-1-[2-(azetidin-3-ylamino)-ethyl]-2-oxo-pyrrolidin-3-ylidenemethyl]-8-oxo-5-thia-1-aza-bicyclo[4.2.0]oct-2-ene-2-carboxylic acid

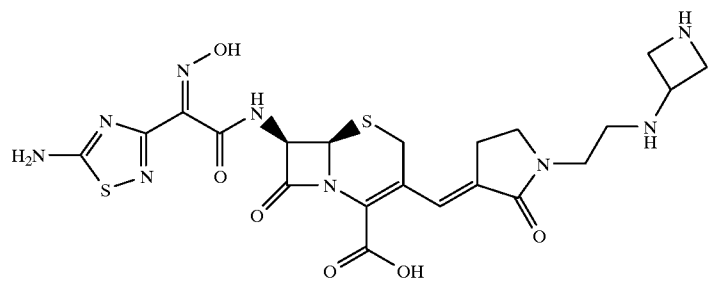

17.19. (6R,7R)-7-[(Z)-2-(5-Amino-[1,2,4]thiadiazol-3-yl)-2-hydroxyimino-acetylamino]-3-[(E)-1-carbamimidoylmethyl-2-oxo-pyrrolidin-3-ylidenemethyl]-8-oxo-5-thia-1-aza-bicyclo[4.2.0]oct-2-ene-2-carboxylic acid

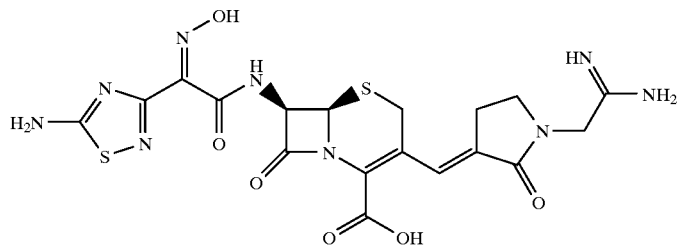

17.20. (6R,7R)-7-[(Z)-2-(5-Amino-[1,2,4]thiadiazol-3-yl)-2-hydroxyimino-acetylamino]-3-[(E)-1-(1-iminomethyl-azetidin-3-yl)-2-oxo-pyrrolidin-3-ylidenemethyl]-8-oxo-5-thia-1-aza-bicyclo[4.2.0]oct-2-ene-2-carboxylic acid

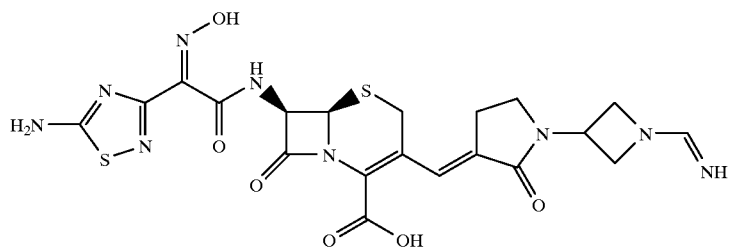

17.21. (6R,7R)-7-[(Z)-2-(5-Amino-[1,2,4]thiadiazol-3-yl)-2-hydroxyimino-acetylamino]-3-[(E)-1-(1-carbamimidoyl-azetidin-3-yl)-2-oxo-pyrrolidin-3-ylidenemethyl]-8-oxo-5-thia-1-aza-bicyclo[4.2.0]oct-2-ene-2-carboxylic acid

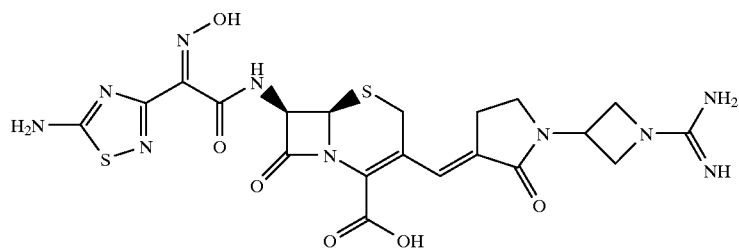

17.22. (6R,7R)-7-[(Z)-2-(5-Amino-[1,2,4]thiadiazol-3-yl)-2-hydroxyimino-acetylamino]-3-[(E)-1-(1-iminomethyl-azetidin-3-ylmethyl)-2-oxo-pyrrolidin-3-ylidenemethyl]-8-oxo-5-thia-1-aza-bicyclo[4.2.0]oct-2-ene-2-carboxylic acid

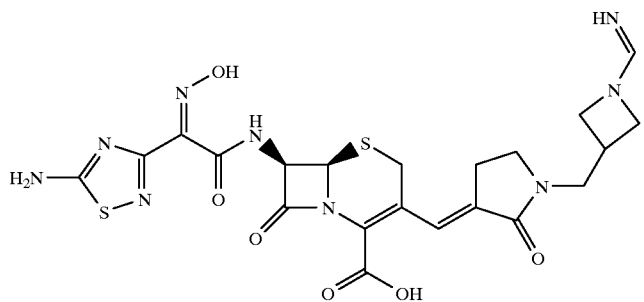

17.23. (6R,7R)-7-[(Z)-2-(5-Amino-[1,2,4]thiadiazol-3-yl)-2-hydroxyimino-acetylamino]-3-[(E)-1-(1-carbamimidoyl-azetidin-3-ylmethyl)-2-oxo-pyrrolidin-3-ylidenemethyl]-8-oxo-5-thia-1-aza-bicyclo[4.2.0]oct-2-ene-2-carboxylic acid

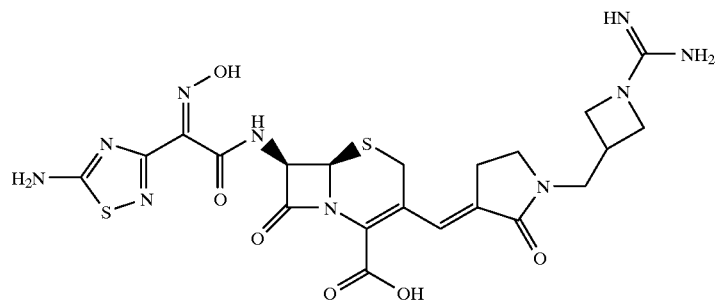

17.24. (6R,7R)-7-[(Z)-2-(2-Amino-thiazol-4-yl)-2-hydroxyimino-acetylamino]-3-[(E)-5'-hydroxymethyl-2-oxo-[1,3']bipyrrolidinyl-3-ylidenemethyl]-8-oxo-5-thia-1-aza-bicyclo[4.2.0]oct-2-ene-2-carboxylic acid

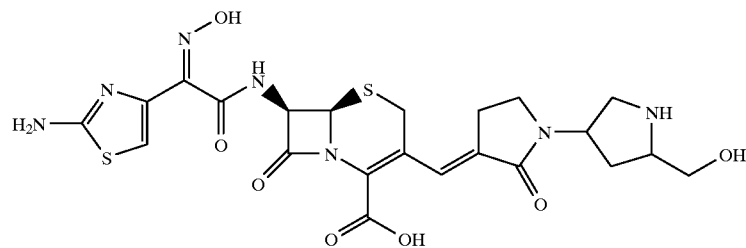

17.25. (6R,7R)-3-[(E)-5'-Aminomethyl-2-oxo-[1,3']bipyrrolidinyl-3-ylidenemethyl]-7-[(Z)-2-(2-amino-thiazol-4-yl)-2-hydroxyimino-acetylamino]-8-oxo-5-thia-1-aza-bicyclo[4.2.0]oct-2-ene-2-carboxylic acid

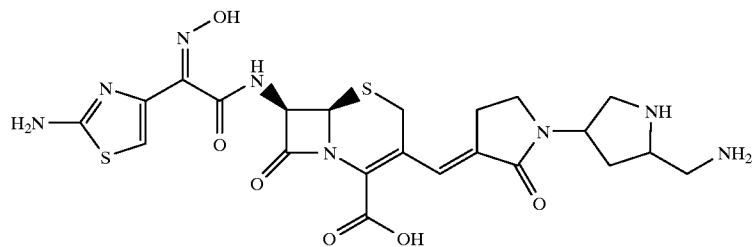

17.26. (6R,7R)-7-[(Z)-2-(2-Amino-thiazol-4-yl)-2-hydroxyimino-acetylamino]-8-oxo-3-[(E)-2-oxo-5'-pyridin-1-ium-1-ylmethyl-[1,3']bipyrrolidinyl-3-ylidenemethyl]-5-thia-1-aza-bicyclo[4.2.0]oct-2-ene-2-carboxylate

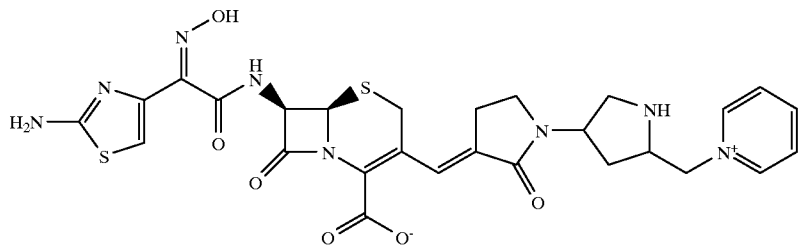

17.27. (6R,7R)-7-[(Z)-2-(2-Amino-thiazol-4-yl)-2-hydroxyimino-acetylaminol-3-[(E)-5'-(1-hydroxy-3-methylamino-propyl)-2-oxo-[1,3']bipyrrolidinyl-3-ylidenemethyl]-8-oxo-5-thia-1-aza-bicyclo[4.2.0]oct-2-ene-2-carboxylic acid

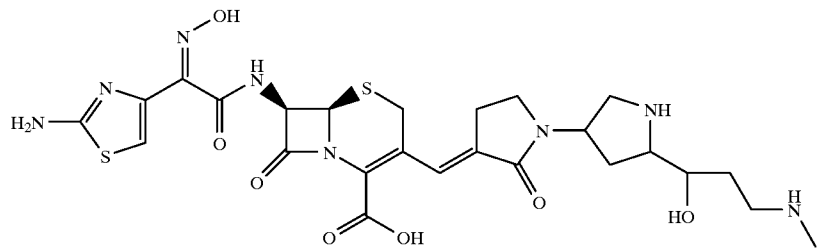

17.28. (6R,7R)-7-[(Z)-2-(2-Amino-thiazol-4-yl)-2-hydroxyimino-acetylamino]-3-[(E)-4'-hydroxy-2-oxo-[1,3']bipyrrolidinyl-3-ylidenemethyl]-8-oxo-5-thia-1-aza-bicyclo[4.2.0]oct-2-ene-2-carboxylic acid

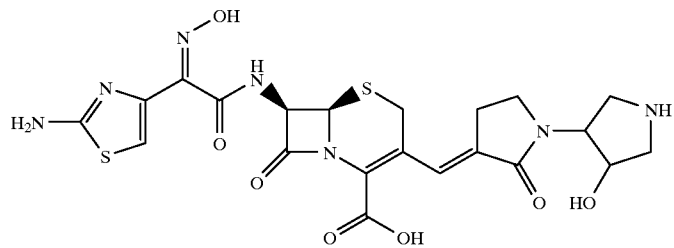

17.29. (6R,7R)-7-[(Z)-2-(2-Amino-thiazol-4-yl)-2-hydroxyimino-acetylamino]-3-[(E)-5'-(hydroxy-pyrrolidin-2-yl-methyl)-2-oxo-[1,3']bipyrrolidinyl-3-ylidenemethyl]-8-oxo-5-thia-1-aza-bicyclo[4.2.0]oct-2-ene-2-carboxylic acid

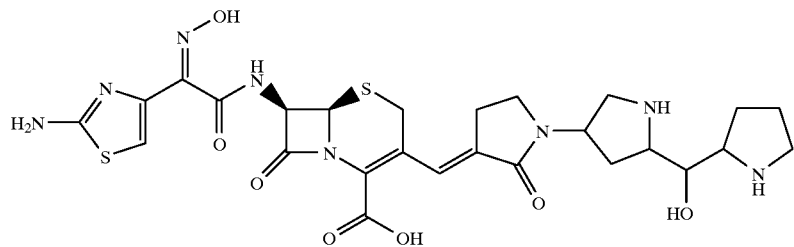

17.30. (6R,7R)-7-[(Z)-2-(2-Amino-thiazol-4-yl)-2-hydroxyimino-acetylaminol-8-oxo-3-[(E)-2-oxo-1-pyrrolidin-3-ylmethyl-pyrrolidin-3-ylidenemethyl]-5-thia-1-aza-bicyclo[4.2.0]oct-2-ene-2-carboxylic acid

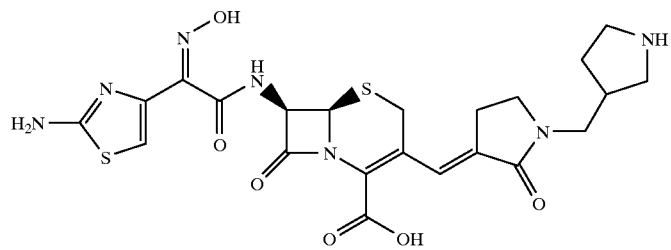

17.31. (6R,7R)-7-[(Z)-2-(2-Amino-thiazol-4-yl)-2-hydroxyimino-acetylamino]-3-[(E)-1-azetidin-3-ylmethyl-2-oxo-pyrrolidin-3-ylidenemethyl]-8-oxo-5-thia-1-aza-bicyclo[4.2.0]oct-2-ene-2-carboxylic acid

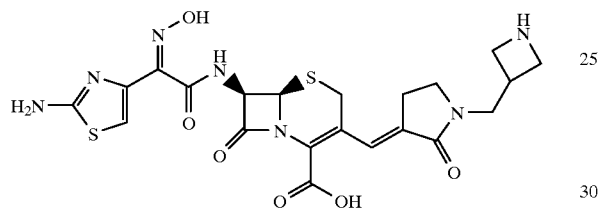

17.32. (6R,7R)-7-[(Z)-2-(2-Amino-thiazol-4-yl)-2-hydroxyimino-acetylamino]-3-[(E)-1'-azetidin-3-ylmethyl-2-oxo-[1,3']bipyrrolidinyl-3-ylidenemethyl]-8-oxo-5-thia-1-aza-bicyclo[4.2.0]oct-2-ene-2-carboxylic acid

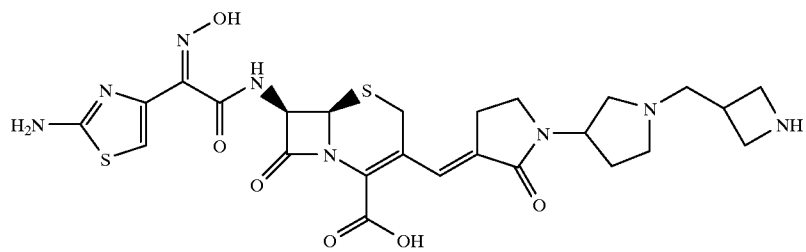

17.33. (6R,7R)-7-[(Z)-2-(2-Amino-thiazol-4-yl)-2-hydroxyimino-acetylamino]-8-oxo-3-[(E)-2-oxo-1'-pyrrolidin-2-ylmethyl-[1,3']bipyrrolidinyl-3-ylidenemethyl]-5-thia-1-aza-bicyclo[4.2.0]oct-2-ene-2-carboxylic acid

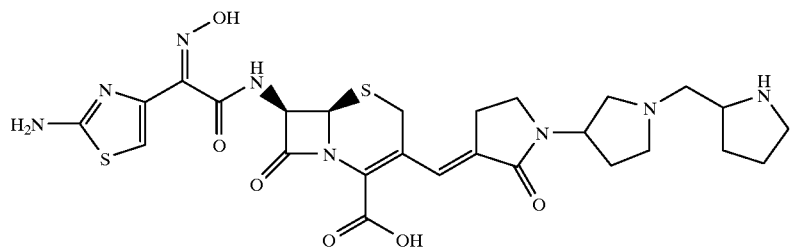

17.34. (6R,7R)-7-[(Z)-2-(2-Amino-thiazol-4-yl)-2-hydroxyimino-acetylamino]-3-[(E)-1-[2-(2-hydroxy-ethylamino)-ethyl]-2-oxo-pyrrolidin-3-ylidenemethyl]-8-oxo-5-thia-1-aza-bicyclo[4.2.0]oct-2-ene-2-carboxylic acid

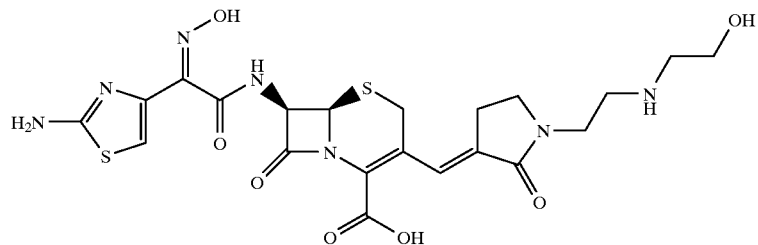

17.35. (6R,7R)-7-[(Z)-2-(2-Amino-thiazol-4-yl)-2-hydroxyimino-acetylamino]-3-[(E)- 1-(2-methylamino-ethyl)-2-oxo-pyrrolidin-3-ylidenemethyl]-8-oxo-5-thia-1-aza-bicyclo[4.2.0]oct-2-ene-2-carboxylic acid

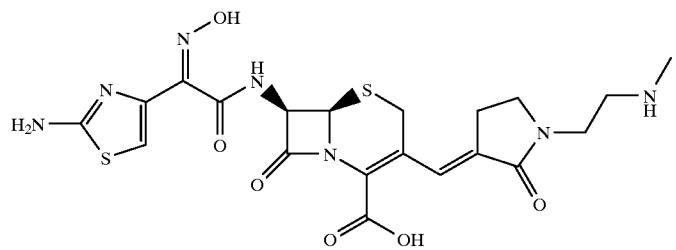

17.36. (6R,7R)-7-[(Z)-2-(2-Amino-thiazol-4-yl)-2-hydroxyimino-acetylamino]-3-[(E)-1-(2-cyclopropylamino-ethyl)-2-oxo-pyrrolidin-3-ylidenemethyl]-8-oxo-5-thia-1-aza-bicyclo[4.2.0]oct-2-ene-2-carboxylic acid

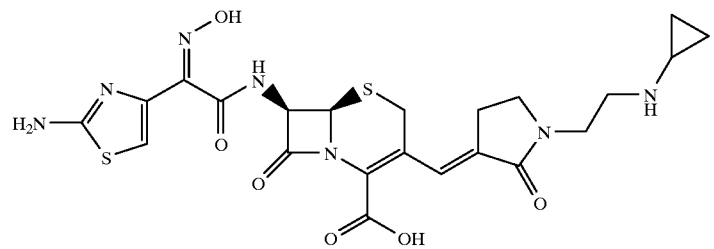

17.37. (6R,7R)-7-[(Z)-2-(2-Amino-thiazol-4-yl)-2-hydroxyimino-acetylaminol]-3-[(E)-1-[2-(iminomethylamino)-ethyl]-2-oxo-pyrrolidin-3-ylidenemethyl]-8-oxo-5-thia-1-aza-bicyclo[4.2.0]oct-2-ene-2-carboxylic acid

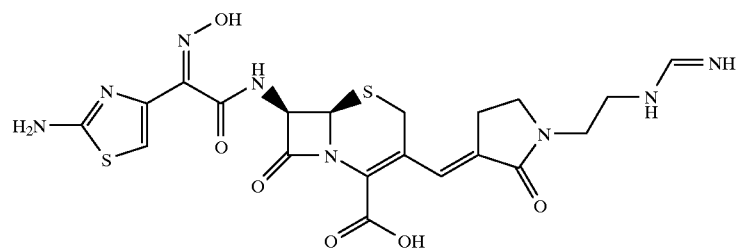

17.38. (6R,7R)-7-[(Z)-2-(2-Amino-thiazol-4-yl)-2-hydroxyimino-acetylamino]-3-[(E)-1-(2-guanidino-ethyl)-2-oxo-pyrrolidin-3-ylidenemethyl]-8-oxo-5-thia-1-aza-bicyclo[4.2.0]oct-2-ene-2-carboxylic acid

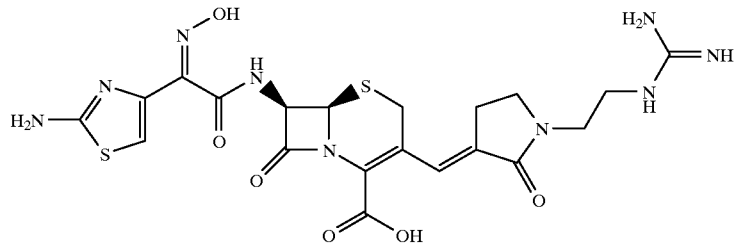

17.39. (6R,7R)-7-[(Z)-2-(2-Amino-thiazol-4-yl)-2-hydroxyimino-acetylamino]-8-oxo-3-[(E)-2-oxo-1-(2-piperazin-1-yl-ethyl)-pyrrolidin-3-ylidenemethyl]-5-thia-1-aza-bicyclo[4.2.0]oct-2-ene-2-carboxylic acid

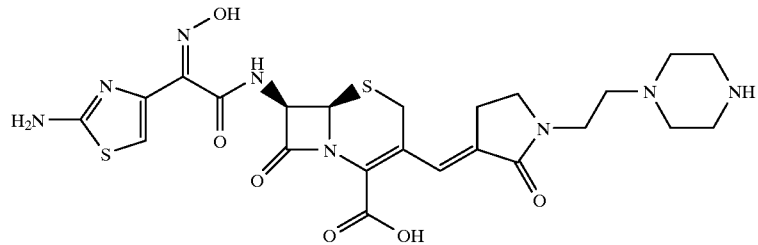

17.40. (6R,7R)-7-[(Z)-2-(2-Amino-thiazol-4-yl)-2-hydroxyimino-acetylamino]-8-oxo-3-[(E)-2-oxo-1-[2-(pyrrolidin-3-ylamino)-ethyl]-pyrrolidin-3-ylidenemethyl]-5-thia-1-aza-bicyclo[4.2.0]oct-2-ene-2-carboxylic acid

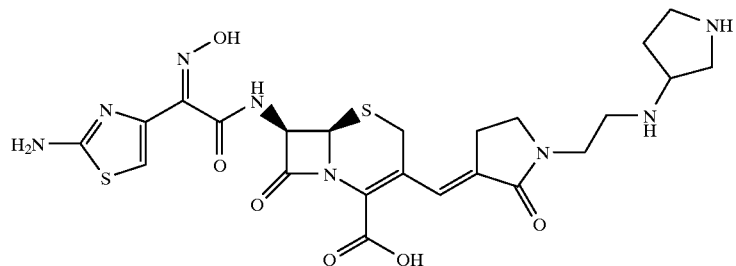

17.41. (6R,7R)-7-[(Z)-2-(2-Amino-thiazol-4-yl)-2-hydroxyimino-acetylamino]-3-[(E)-1-[2-(azetidin-3-ylamino)-ethyl]-2-oxo-pyrrolidin-3-yidenemethyl]-8-oxo-5-thia-1-aza-bicyclo[4.2.0]oct-2-ene-2-carboxylic acid

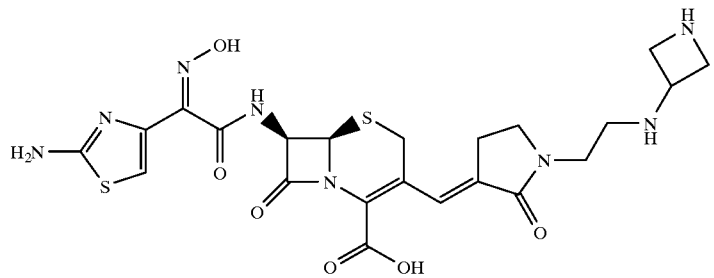

17.42. (6R,7R)-7-[(Z)-2-(2-Amino-thiazol-4-yl)-2-hydroxyimino-acetylamino]-3-[(E)-1-carbamimidoylmethyl-2-oxo-pyrrolidin-3-ylidenemethyl]-8-oxo-5-thia-1-aza-bicyclo[4.2.0]oct-2-ene-2-carboxylic acid

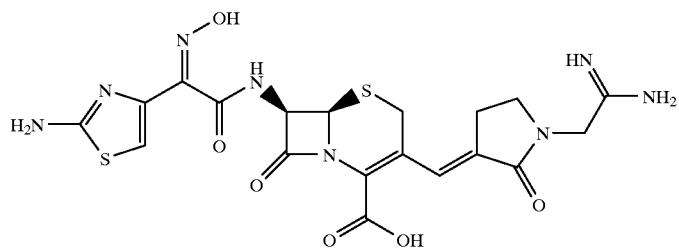

17.43. (6R,7R)-7-[(Z)-2-(2-Amino-thiazol-4-yl)-2-hydroxyimino-acetylamino]-3-[(E)-1-(1-iminomethyl-azetidin-3-yl)-2-oxo-pyrrolidin-3-ylidenemethyl]-8-oxo-5-thia-1-aza-bicyclo[4.2.0]oct-2-ene-2-carboxylic acid

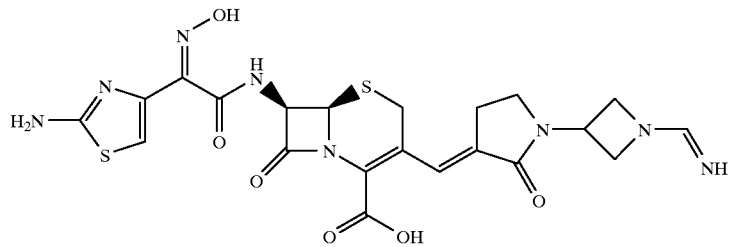

17.44. (6R,7R)-7-[(Z)-2-(2-Amino-thiazol-4-yl)-2-hydroxyimino-acetylaminol-3-[(E)-1-(carbamimidoyl-azetidin-3-yl)-2-oxo-pyrrolidin-3-ylidenemethyl]-8-oxo-5-thia-1-aza-bicyclo[4.2.0]oct-2-ene-2-carboxylic acid

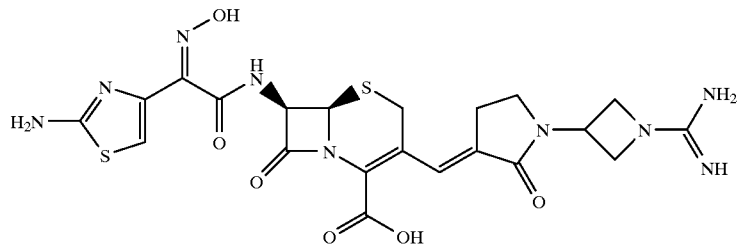

17.45. (6R,7R)-7-[(Z)-2-(2-Amino-thiazol-4-yl)-2-hydroxyimino-acetylamino]-3-[(E)-1-(1-iminomethyl-azetidin-3- methyl)-2-oxo-pyrrolidin-3-ylidenemethyl]-8-oxo-5-thia-1-aza-bicyclo[4.2.0]oct-2-ene-2-carboxylic acid 17.46. (6R,7R)-7-[(Z)-2-(2-Amino-thiazol-4-yl)-2-hydroxyimino-acetylamino]-3-[(E)-1-(1-carbamimidoyl-azetidin-3-ylmethyl)-2-oxo-pyrrolidin-3-ylidenemethyl]-8-oxo-5-thia-1-aza-bicyclo[4.2.0]oct-2-ene-2-carboxylic acid

We claim:

1. A compound having the formula wherein

X is CH or N;
R$^1$ is hydrogen or cyclopentyl;
R$^2$ is selected from the group consisting of and R$^3$ is hydrogen, an alkalimetal ion or a tertiary ammonium group;

R$^4$ is hydrogen, an amino protecting group, pyrrolidin-2-ylmethyl, azetidin-3-ylmethyl, iminomethyl, or 1-carbamimidoyl;

R$^5$ is hydrogen, dialkylcarbamoyl, ω-hydroxyalkyl, ω-aminoalkyl, 1-hydroxy-3-aminomethyl-propyl or (hydroxy)-(pyrrolidin-2-yl)methyl;

R$^6$ is hydrogen, trifluoromethyl or hydroxy; and

R$^7$ is alkyl, ω-hydroxy-alkyl, cycloalkyl, 3-pyrrolidinyl, 3-azetidinyl, iminomethyl or 1-carbamimidoyl;

as well as esters thereof which are readily hydrolyzable in vivo, pharmaceutically acceptable salts of said compounds and hydrates of the compounds of formula I and of their esters and salts.

2. The compound of claim 1, wherein X is N.

3. The compound of claim 2, wherein R$^1$ is hydrogen.

4. The compound of claim 3, wherein each of R$^4$, R$^5$, and R$^6$ are hydrogen.

5. The compound of claim 4, wherein R$^2$ is selected from the group consisting of

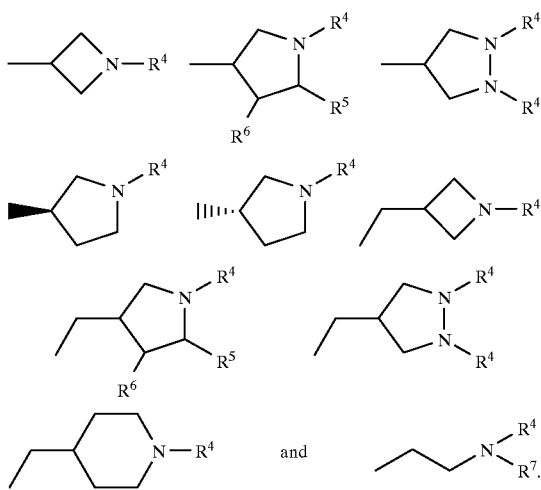

6. The compound of claim 5, wherein R² is selected from the group consisting of

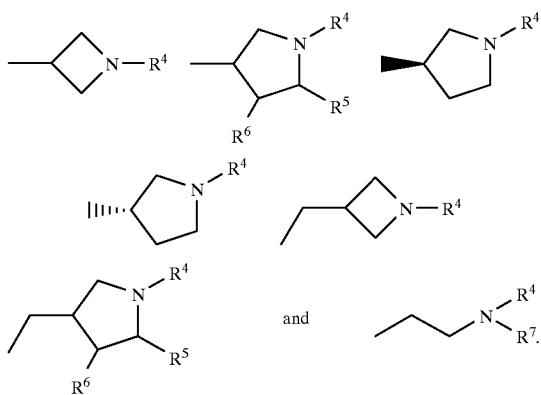

7. The compound of claim 6, wherein R² is selected from the group consisting of

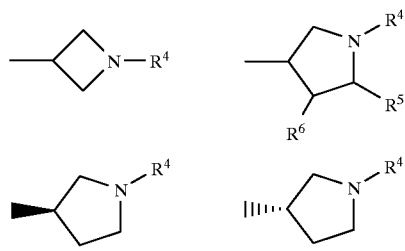

8. The compound of claim 7, wherein R² is

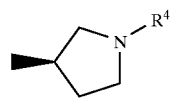

9. The compound of claim 8, (6R,7R)-7-[(Z)-2-(5-Amino-[1,2,4]thiadiazol-3-yl)-2-hydroxyimino-acetylamino]-8-oxo-3-[(E)-(R)-2-oxo-[1,3']bipyrrolidinyl-3-ylidenemethyl]-5-thia-1-aza-bicyclo[4.2.0]oct-2-ene-2-carboxylic acid.

10. The compound of claim 7, wherein R² is

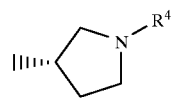

11. The compound of claim 10, (6R,7R)-7-[(Z)-2-(5-Amino-[1,2,4]thiadiazol-3-yl)-2-hydroxyimino-acetylamino]-8-oxo-3-[(E)-(S)-2-oxo-[1,3'bipyrrolidinyl-3-ylidenemethyl]-5-thia-1-aza-bicyclo[4.2.0]oct-2-ene-2-carboxylic acid.

12. The compound of claim 7, wherein R² is

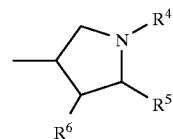

13. The compound of claim 12, (6R,7R)-7-[(Z)-2-(5-Amino-[1,2,4]thiadiazol-3-yl)-2-hydroxyimino-acetylamino]-8-oxo-3-[(E)-(R)- and -(S)-2-oxo-[1,3]bipyrrolidinyl-3-ylidenemethyl]-5-thia-1-aza-bicyclo[4.2.0]oct-2-ene-2-carboxylic acid.

14. The compound of claim 7, wherein R² is

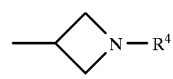

15. The compound of claim 14, (6R,7R)-7-[(Z)-2-(5-Amino-[1,2,4]thiadiazol-3-yl)-2-hydroxyimino-acetylamino]-3-[(E)-1-azetidin-3-yl-2-oxo-pyrrolidin-3-ylidenemethyl]-8-oxo-5-thia-1-aza-bicyclo[4.2.0]oct-2-ene-2-carboxylic acid.

16. The compound of claim 3 wherein R² is

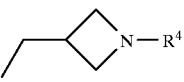

17. The compound of claim 16, (6R,7R)-7-[(Z)-2-(5-Amino-[1,2,4]thiadiazol-3-yl)-2-hydroxyimino-acetylamino]-3-[(E)-1-azetidin-3-ylmethyl-2-oxo-pyrrolidin-3-ylidenemethyl]-8-oxo-5-thia-1-aza-bicyclo[4.2.0]oct-2-ene-2-carboxylic acid.

18. The compound of claim 3, wherein R² is

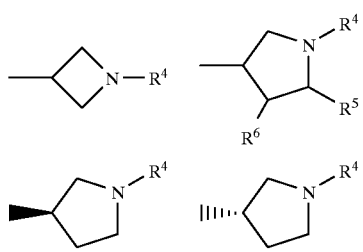

19. The compound of claim 18, wherein R⁴ is hydrogen, iminomethyl, or 1-carbamimidoyl; R⁵ is hydrogen or ω-hydroxyalkyl; and R⁶ is hydrogen.

20. The compound of claim 19, wherein R⁴ is iminomethyl and R⁵ is hydrogen.

21. The compound of claim 20, (6R,7R)-7-[(Z)-2-(5-Amino-[1,2,4]thiadiazol-3-yl)-2-hydroxyimino-acetylamino]-3-[(E)-(R)-1'-iminomethyl-2-oxo-[1,3'] bipyrrolidinyl-3-ylidenemethyl]-8-oxo-5-thia-1-aza-bicyclo [4.2.0]oct-2-ene-2-carboxylic acid.

22. The compound of claim 19, wherein $R^4$ is 1-carbamimidoyl and $R^5$ is hydrogen.

23. The compound of claim 22, (6R,7R)-7-[(Z)-2-(5-Amino-[1,2,4]thiadiazol-3-yl)-2-hydroxyimino-acetylaminol-3-[(E)-(R)-1'-carbamimidoyl-2-oxo-[1,3'] bipyrrolidinyl-3-ylidenemethyl]-8-oxo-5-thia-1-aza-bicyclo [4.2.0]oct-2-ene-2-carboxylic acid.

24. The compound of claim 19, wherein $R^4$ is hydrogen and $R^5$ is ω-hydroxyalkyl.

25. The compound of claim 24, (6R,7R)-7-[(Z)-2-(5-Amino-[1,2,4]thiadiazol-3-yl)-2-hydroxyimino-acetylamino]-3-[(E)-5'-hydroxymethyl-2-oxo-[1,3'] bipyrrolidinyl-3-ylidenemethyl]-8-oxo-5-thia-1-aza-bicyclo [4.2.0]oct-2-ene-2-carboxylic acid.

26. The compound of claim 2, wherein $R^1$ is cyclopentyl.

27. The compound of claim 26, wherein $R^2$ is

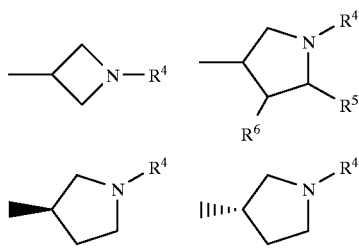

28. The compound of claim 27, wherein $R^2$ is

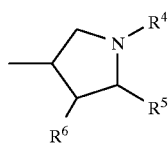

29. The compound of claim 28, (6R,7R)-7-[(Z)-2-(5-Amino-[1,2,4]thiadiazol-3-yl)-2-cyclopentyloxyimino-acetylamino]-8-oxo-3-[(E)-(R)- and -(S)-2-oxo-1,3'] bipyrrolidinyl-3-ylidenemethyl]-5-thia-1-aza-bicyclo[4.2.0] oct-2-ene-2-carboxylic acid.

30. The compound of claim 27, wherein $R^2$ is

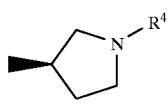

31. The compound of claim 30, (6R,7R)-7-[(Z)-2-(5-Amino-[1,2,4]thiadiazol-3-yl)-2-cyclopentyloxyimino-acetylamino]-8-oxo-3-[(E)-(R)-2-oxo-1,3]bipyrrolidinyl-3-ylidenemethyl]-5-thia-1-aza-bicyclo[4.2.0]oct-2-ene-2-carboxylic acid.

32. The compound of claim 1, wherein X is CH.

33. The compound of claim 32, wherein $R^1$ is hydrogen.

34. The compound of claim 33, wherein $R^2$ is

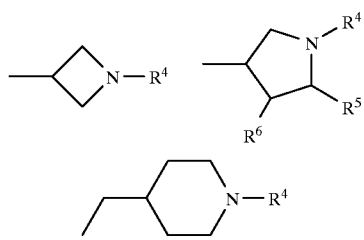

35. The compound of claim 34, wherein $R^2$ is

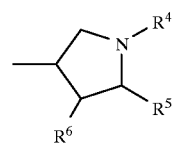

36. The compound of claim 35, wherein each of $R^4$, $R^5$, and $R^6$ are hydrogen.

37. The compound of claim 36, (6R,7R)-7-[(Z)-2-(2-Amino-thiazol-4-yl)-2-hydroxyimino-acetylamino]-8-oxo-3-[(E)-(R)- and (S)-2-oxo-[1,3']bipyrrolidnyl-3-ylidenemethyl]-5-thia-1-aza-bicyclo[4.2.0oct-2-ene-2-carboxylic acid.

38. The compound of claim 34, wherein $R^2$ is

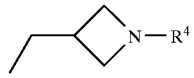

39. The compound of claim 38, (6R,7R)-7-[(Z)-2-(2-Amino-thiazol-4-yl)-2-hydroxyimino-acetylamino]-3-[(E)-1-azetidin-3-ylmethyl-2-oxo-pyrrolidnyl-3-ylidenemethyl]-8-oxo-5-thia-1-aza-bicyclo[4.2.0]oct-2-ene-2-carboxylic acid.

40. The compound of claim 34, wherein $R^2$ is

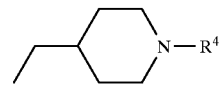

41. The compound of claim 40, (6R,7R)-7-[(Z)-2-(2-Amino-thiazol-4-yl)-2-hydroxyimino-acetylamino]-3-[(E)-1-piperidin-4-ylmethyl-pyrrolin-3-ylidenemethyl]-5-thia-1-aza-bicyclo[4.2.0]oct-2-ene-2-carboxylic acid.

42. The compound of claim 32, wherein $R^1$ is cyclopentyl.

43. The compound of claim 42, wherein $R^2$ is

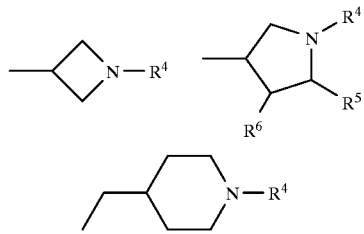

44. The compound of claim 43, wherein R² is

[structure: methyl-azetidine-N-R⁴]

45. The compound of claim 44, wherein R⁴ is an amino protecting group or hydrogen.

46. The compound of claim 45, wherein R⁴ is an amino protecting group.

47. The compound of claim 46, (6R,7R)-3-[(E)-1-(1-allyloxycarbonylazetidin-3-yl)-2-oxo-pyrrolin-3-ylidenemethyl]-7-[(Z)-2-(2-amino-thiazol-4-yl)-2-cyclopentyloxyimino-acetylamino]-8-oxo-5-thia-1-aza-bicyclo[4.2.0]oct-2-ene-2-carboxylic acid.

48. The compound of claim 45, wherein R⁴ is hydrogen.

49. The compound of claim 48, (6R,7R)-7-[(Z)-2-(2-amino-thiazol-4-yl)-2-cyclopentyloxyimino-acetylamino]-3-[(E)-1-azetidin-3-yl-2-oxo-pyrrolin-3-ylidenemethyl]-]-8-oxo-5-thia-1-aza-bicyclo[4.2.0]oct-2-ene-2-carboxylic acid.

50. The compound of claim 43, wherein R² is

[structure: ethyl-azetidine-N-R⁴]

51. The compound of claim 50, wherein R⁴ is an amino protecting group or hydrogen.

52. The compound of claim 51, wherein R⁴ is an amino protecting group.

53. The compound of claim 52, (6R,7R)-3-[(E)-1-(1-allyloxycarbonylpiperidin-4-ylmethyl)-2-oxo-pyrrolin-3-ylidenemethyl]-7-[(Z)-2-(2-aminothiazol-4-yl)-2-cyclopentyloxyimino-acetylaminol-8-oxo-5-thia-1-aza-bicyclo[4.2.0]oct-2-ene-2-carboxylic acid.

54. The compound of claim 51, wherein R⁴ is hydrogen.

55. The compound of claim 54, (6R,7R)-7-[(Z)-2-(2-amino-thiazol-4-yl)-2-cyclopentyloxyimino-acetylamino]-3-[(E)-2-oxo-1-piperidin-4ylmethylpyrrolin-3-ylidenemethyl]-]-8-oxo-5-thia-1-aza-bicyclo[4.2.0]oct-2-ene-2-carboxylic acid.

56. The compound of claim 43, wherein R² is

[structure: pyrrolidine with N-R⁴, R⁵, R⁶]

57. The compound of claim 56, wherein R⁴ is an amino protecting group or hydrogen.

58. The compound of claim 57, wherein R⁴ is an amino protecting group.

59. The compound of claim 58, (6R,7R)-3-[(E)-(R)- and -(S)-1'-allyloxycarbonyl-2-oxo-[1,3']bipyrrolidinyl-3-ylidenemethyl]-7-[(Z)-2-(2-amino-thiazol-4-yl)-2-cyclopentyloxyimino-acetylamino]-8-oxo-5-thia-1-aza-bicyclo[4.2.0]oct-2-ene-2-carboxylic acid.

60. The compound of claim 57, wherein R⁴ is hydrogen.

61. The compound of claim 60, (6R,7R)-7-[(Z)-2-(2-amino-thiazol-4-yl)-2-cyclopentyloxyimino-acetylamino]-8-oxo-3-[(E)-(R)- and -(S)-2-oxo-[1,3']bipyrrolinyl-3-ylidenemethyl]-]-5-thia-1-aza-bicyclo[4.2.0]oct-2-ene-2-carboxylic acid.

62. A pharmaceutical composition for treating infections caused by methicillin resistant *Staphylococcus aureus* (MRSA) and *Pseudomonas aeruginosa* comprising a therapeutically effective amount of a compound of the formula

I

[structure of formula I with R¹, R², R³, X]

wherein

X is CH or N;

R¹ is hydrogen or cyclopentyl;

R² is selected from the group consisting of formula

[structures showing various R² groups with R⁴, R⁵, R⁶, R⁷ substituents]

and

R³ is hydrogen, an alkalimetal ion or a tertiary ammonium group;

R⁴ is hydrogen, an amino protecting group, pyrrolidin-2-ylmethyl, azetidin-3-ylmethyl, iminomethyl, or 1-carbamimidoyl;

R⁵ is hydrogen, dialkylcarbamoyl, ω-hydroxyalkyl, ω-aminoalkyl, 1-hydroxy-3-aminomethyl-propyl or (hydroxy)-(pyrrolidin-2-yl)methyl;

R⁶ is hydrogen, trifluoromethyl or hydroxy; and

R⁷ is alkyl, ω-hydroxy-alkyl, cycloalkyl, 3-pyrrolidinyl, 3-azetidinyl, iminomethyl or 1-carbamimidoyl;

as well as esters thereof which are readily hydrolyzable in vivo, pharmaceutically acceptable salts of said compounds and hydrates of the compounds of formula I and of their esters and salts, and a pharmaceutically inert carrier.

63. A method of treating infections caused by methicillin resistant *Staphylococcus aureus* (MRSA) and *Pseudomonas aeruginosa* in a mammal comprising administering to said mammal in need of such treatment a compound of the formula

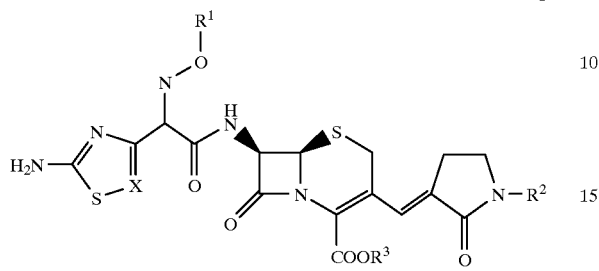

I wherein
X is CH or N;
$R^1$ is hydrogen or cyclopentyl;
$R^2$ is selected from the group consisting of formula

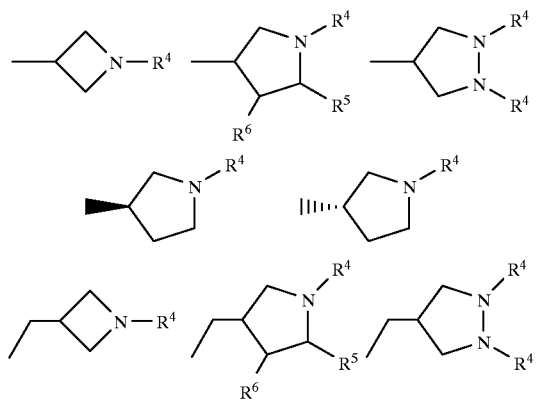

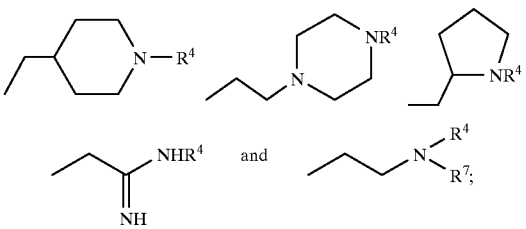

$R^3$ is hydrogen, an alkalimetal ion or a tertiary ammonium group;
$R^4$ is hydrogen, an amino protecting group, pyrrolidin-2-ylmethyl, azetidin-3-ylmethyl, iminomethyl, or 1-carbamimidoyl;
$R^5$ is hydrogen, dialkylcarbamoyl, ω-hydroxyalkyl, ω-aminoalkyl, 1-hydroxy-3-aminomethyl-propyl or (hydroxy)-(pyrrolidin-2-yl)methyl;
$R^6$ is hydrogen, trifluoromethyl or hydroxy; and
$R^7$ is alkyl, ω-hydroxy-alkyl, cycloalkyl, 3-pyrrolidinyl, 3-azetidinyl, iminomethyl or 1-carbamimidoyl;

as well as esters thereof which are readily hydrolyzable in vivo, pharmaceutically acceptable salts of said compounds and hydrates of the compounds of formula I and of their esters and salts in an amount which is effective in treating said infections.

64. A compound which is (6R,7R)-7-[(Z)-2-(5-Amino-[1,2,4]thiadiazol-3-yl)-2-hydroxyimino-acetylamino]-8-oxo-3-[(E)-2-oxo-5'-pyridin-1-ium-1-ylmethyl-[1,3']bipyrrolid-3-ylidenemethyl]-5-thia-1-aza-bicyclo[4.2.0]oct-2-ene-2-carboxylate.

65. A compound which is (6R,7R)-7-[(Z)-2-(2-Amino-thiazol-4-yl)-2-hydroxyiminoacetylamino]-8-oxo-3-[(E)-2-oxo-5'-pyridin-1-ium-1-ylmethyl-[1,3']bipyrrolidinyl-3-ylidenemethyl]-5-thia-1-aza-bicyclo[4.2.0]oct-2-ene-2-carboxylate.

* * * * *

UNITED STATES PATENT AND TRADEMARK OFFICE
CERTIFICATE OF CORRECTION

PATENT NO. : 5,981,519
DATED : November 9, 1999
INVENTOR(S) : Angehrn, et al.

It is certified that error appears in the above-indentified patent and that said Letters Patent is hereby corrected as shown below:

IN THE CLAIMS:

Claim 13, Column 60, line 24: "[1,3]" should read --- [1,3'] --- .

Claim 37, Column 62, line 28: "[4.2.0oct" should read --- [4.2.0]oct --- .

Claim 53, Column 63, line 34: "acetylaminol" should read --- acetylamino] --- .

Signed and Sealed this

Twenty-eighth Day of November, 2000

Attest:

Q. TODD DICKINSON

*Attesting Officer*      *Director of Patents and Trademarks*